(12) United States Patent
Merchant et al.

(10) Patent No.: US 10,881,395 B2
(45) Date of Patent: Jan. 5, 2021

(54) BUTTRESS ATTACHMENT FEATURES FOR SURGICAL STAPLING APPARATUS

(71) Applicant: Covidien LP, Mansfield, MA (US)

(72) Inventors: Rahim R. Merchant, Hamden, CT (US); Gerald N. Hodgkinson, Guilford, CT (US); Danny Berry, Hamden, CT (US); Sally L. Carter, Nashua, NH (US)

(73) Assignee: COVIDIEN LP, Mansfield, MA (US)

( * ) Notice: Subject to any disclaimer, the term of this patent is extended or adjusted under 35 U.S.C. 154(b) by 240 days.

(21) Appl. No.: 15/939,535

(22) Filed: Mar. 29, 2018

(65) Prior Publication Data

US 2018/0214147 A1     Aug. 2, 2018

Related U.S. Application Data

(63) Continuation of application No. 13/942,822, filed on Jul. 16, 2013, now abandoned.

(60) Provisional application No. 61/684,846, filed on Aug. 20, 2012.

(51) Int. Cl.
*A61B 17/064* (2006.01)
*A61B 17/072* (2006.01)
*A61B 17/06* (2006.01)
*A61B 17/115* (2006.01)

(52) U.S. Cl.
CPC ...... *A61B 17/064* (2013.01); *A61B 17/07292* (2013.01); *A61B 17/07207* (2013.01); *A61B 17/1155* (2013.01); *A61B 2017/06033* (2013.01)

(58) Field of Classification Search
None
See application file for complete search history.

(56) References Cited

U.S. PATENT DOCUMENTS

| | | | |
|---|---|---|---|
| 3,054,406 A | 9/1962 | Usher | |
| 3,079,606 A | 3/1963 | Bobrov et al. | |
| 3,124,136 A | 3/1964 | Usher | |
| 3,364,200 A | 1/1968 | Ashton et al. | |
| 3,490,675 A | 1/1970 | Green et al. | |
| 3,499,591 A | 3/1970 | Green | |

(Continued)

FOREIGN PATENT DOCUMENTS

| CA | 2282761 A1 | 9/1998 |
|---|---|---|
| CN | 101310680 A | 11/2008 |

(Continued)

OTHER PUBLICATIONS

Extended European Search Report corresponding to Patent Application EP 12196912.5 dated Feb. 1, 2016.

(Continued)

*Primary Examiner* — Nathaniel C Chukwurah
*Assistant Examiner* — Mobeen Ahmed

(57) ABSTRACT

An end effector assembly for use with a surgical stapler, comprising a staple cartridge having a tissue contacting surface, an anvil plate having a tissue contacting surface, a buttress material releasably disposed on the tissue contacting surfaces of each of the staple cartridge and the anvil plate, and an epoxy positioned onto the tissue contacting surfaces of each of the staple cartridge and anvil plate defining an attachment zone configured to retain the respective buttress material atop the respective tissue contacting surfaces.

16 Claims, 17 Drawing Sheets

(56) References Cited

U.S. PATENT DOCUMENTS

| | | | |
|---|---|---|---|
| 3,797,494 A | 3/1974 | Zaffaroni | |
| 3,939,068 A | 2/1976 | Wendt et al. | |
| 3,948,666 A | 4/1976 | Kitanishi et al. | |
| 4,064,062 A | 12/1977 | Yurko | |
| 4,166,800 A | 9/1979 | Fong | |
| 4,282,236 A | 8/1981 | Broom | |
| 4,347,847 A | 9/1982 | Usher | |
| 4,354,628 A | 10/1982 | Green | |
| 4,416,698 A | 11/1983 | McCorsley, III | |
| 4,429,695 A | 2/1984 | Green | |
| 4,452,245 A | 6/1984 | Usher | |
| 4,605,730 A | 8/1986 | Shalaby et al. | |
| 4,626,253 A | 12/1986 | Broadnax, Jr. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,057,334 A | 10/1991 | Vail | |
| 5,065,929 A | 11/1991 | Schulze et al. | |
| 5,112,496 A | 5/1992 | Dhawan et al. | |
| 5,162,430 A | 11/1992 | Rhee et al. | |
| 5,205,459 A | 4/1993 | Brinkerhoff et al. | |
| 5,263,629 A * | 11/1993 | Trumbull | A61B 17/07207 128/898 |
| 5,281,197 A | 1/1994 | Arias et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,324,775 A | 6/1994 | Rhee et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,410,016 A | 4/1995 | Hubbell et al. | |
| 5,425,745 A | 6/1995 | Green et al. | |
| 5,441,193 A * | 8/1995 | Gravener | A61B 17/07207 227/175.1 |
| 5,441,507 A | 8/1995 | Wilk | |
| 5,443,198 A | 8/1995 | Viola et al. | |
| 5,468,253 A | 11/1995 | Bezwada et al. | |
| 5,484,913 A | 1/1996 | Stilwell et al. | |
| 5,503,638 A | 4/1996 | Cooper et al. | |
| 5,514,379 A | 5/1996 | Weissleder et al. | |
| 5,542,594 A | 8/1996 | McKean et al. | |
| 5,543,441 A | 8/1996 | Rhee et al. | |
| 5,549,628 A | 8/1996 | Cooper et al. | |
| 5,550,187 A | 8/1996 | Rhee et al. | |
| 5,575,803 A | 11/1996 | Cooper et al. | |
| 5,645,915 A | 7/1997 | Kranzler et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,752,974 A | 5/1998 | Rhee et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,819,350 A | 10/1998 | Wang | |
| 5,833,695 A | 11/1998 | Yoon | |
| 5,843,096 A | 12/1998 | Igaki et al. | |
| 5,871,135 A | 2/1999 | Williamson, IV et al. | |
| 5,874,500 A | 2/1999 | Rhee et al. | |
| 5,895,412 A | 4/1999 | Tucker | |
| 5,895,415 A | 4/1999 | Chow et al. | |
| 5,902,312 A * | 5/1999 | Frater | A61B 17/07207 606/148 |
| 5,908,427 A * | 6/1999 | McKean | A61B 17/07207 606/139 |
| 5,915,616 A | 6/1999 | Viola et al. | |
| 5,931,847 A | 8/1999 | Bittner et al. | |
| 5,957,363 A | 9/1999 | Heck | |
| 5,964,394 A | 10/1999 | Robertson | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,093,557 A | 7/2000 | Pui et al. | |
| 6,099,551 A | 8/2000 | Gabbay | |
| 6,142,933 A | 11/2000 | Longo et al. | |
| 6,149,667 A | 11/2000 | Hovland et al. | |
| 6,152,943 A | 11/2000 | Sawhney | |
| 6,155,265 A | 12/2000 | Hammerslag | |
| 6,156,677 A | 12/2000 | Brown Reed et al. | |
| 6,165,201 A | 12/2000 | Sawhney et al. | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,530 B1 | 8/2001 | Eldridge et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,309,569 B1 | 10/2001 | Farrar et al. | |
| 6,312,457 B1 | 11/2001 | DiMatteo et al. | |
| 6,312,474 B1 | 11/2001 | Francis et al. | |
| 6,325,810 B1 * | 12/2001 | Hamilton | A61B 17/07207 227/175.1 |
| 6,330,965 B1 | 12/2001 | Milliman et al. | |
| 6,399,362 B1 | 6/2002 | Pui et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,500,777 B1 | 12/2002 | Wiseman et al. | |
| 6,503,257 B2 | 1/2003 | Grant et al. | |
| 6,514,283 B2 | 2/2003 | DiMatteo et al. | |
| 6,514,534 B1 | 2/2003 | Sawhney | |
| 6,517,566 B1 | 2/2003 | Hovland et al. | |
| 6,551,356 B2 | 4/2003 | Rousseau | |
| 6,566,406 B1 | 5/2003 | Pathak et al. | |
| 6,568,398 B2 | 5/2003 | Cohen | |
| 6,590,095 B1 | 7/2003 | Schleicher et al. | |
| 6,592,597 B2 | 7/2003 | Grant et al. | |
| 6,605,294 B2 | 8/2003 | Sawhney | |
| 6,610,006 B1 | 8/2003 | Amid et al. | |
| 6,627,749 B1 | 9/2003 | Kumar | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,656,200 B2 | 12/2003 | Li et al. | |
| 6,669,735 B1 | 12/2003 | Pelissier | |
| 6,673,093 B1 | 1/2004 | Sawhney | |
| 6,677,258 B2 | 1/2004 | Carroll et al. | |
| 6,685,714 B2 | 2/2004 | Rousseau | |
| 6,702,828 B2 | 3/2004 | Whayne | |
| 6,703,047 B2 | 3/2004 | Sawhney et al. | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,746,869 B2 | 6/2004 | Pui et al. | |
| 6,764,720 B2 | 7/2004 | Pui et al. | |
| 6,773,458 B1 | 8/2004 | Brauker et al. | |
| 6,818,018 B1 | 11/2004 | Sawhney | |
| 6,843,252 B2 | 1/2005 | Harrison et al. | |

(56) References Cited

U.S. PATENT DOCUMENTS

| | | |
|---|---|---|
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,565,993 B2 | 7/2009 | Milliman et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |

(56) References Cited

U.S. PATENT DOCUMENTS

| | | |
|---|---|---|
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0091397 A1 | 7/2002 | Chen |
| 2002/0151911 A1 | 10/2002 | Gabbay |
| 2002/0165559 A1* | 11/2002 | Grant ............... A61B 17/07207 606/139 |
| 2002/0165563 A1* | 11/2002 | Grant ............... A61B 17/072 606/151 |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0196668 A1 | 10/2003 | Harrison et al. |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1* | 3/2005 | Bauman ............... A61B 17/072 606/215 |
| 2005/0059997 A1* | 3/2005 | Bauman ............... A61B 17/072 606/219 |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0228446 A1* | 10/2005 | Mooradian ........... A61B 17/115 606/215 |
| 2005/0245965 A1* | 11/2005 | Orban, III ........... A61B 17/115 606/214 |
| 2005/0283256 A1 | 12/2005 | Sommerich et al. |
| 2006/0004407 A1* | 1/2006 | Hiles ................. A61B 17/0644 606/215 |
| 2006/0008505 A1 | 1/2006 | Brandon |

(56) References Cited

U.S. PATENT DOCUMENTS

| | | |
|---|---|---|
| 2006/0025816 A1* | 2/2006 | Shelton, IV ..... A61B 17/07207 606/215 |
| 2006/0085030 A1 | 4/2006 | Bettuchi et al. |
| 2006/0085034 A1 | 4/2006 | Bettuchi |
| 2006/0121266 A1 | 6/2006 | Fandel et al. |
| 2006/0135992 A1* | 6/2006 | Bettuchi .......... A61B 17/07292 606/219 |
| 2006/0173470 A1 | 8/2006 | Oray et al. |
| 2006/0190027 A1 | 8/2006 | Downey |
| 2006/0219752 A1* | 10/2006 | Arad ................ A61B 17/07207 227/176.1 |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1* | 10/2007 | Pace-Floridia ............................ A61B 17/07207 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1* | 11/2008 | Bettuchi ............. A61B 17/068 227/176.1 |
| 2008/0308608 A1* | 12/2008 | Prommersberger ........................ A61B 17/07207 227/176.1 |
| 2008/0314960 A1* | 12/2008 | Marczyk ............ A61B 17/105 227/178.1 |
| 2009/0001121 A1 | 1/2009 | Hess et al. |
| 2009/0001122 A1* | 1/2009 | Prommersberger ........................ A61B 17/07207 227/176.1 |
| 2009/0001130 A1 | 1/2009 | Hess et al. |
| 2009/0031842 A1 | 2/2009 | Kawai et al. |
| 2009/0095791 A1 | 4/2009 | Eskaros et al. |
| 2009/0206125 A1* | 8/2009 | Huitema .......... A61B 17/07292 227/175.1 |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1* | 8/2009 | Huitema .......... A61B 17/07207 227/176.1 |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0065606 A1* | 3/2010 | Stopek ................ A61B 17/068 227/176.1 |
| 2010/0087840 A1 | 4/2010 | Ebersole et al. |
| 2010/0116868 A1 | 5/2010 | Prommersberger |
| 2010/0147921 A1* | 6/2010 | Olson ................ A61B 17/068 227/175.1 |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243708 A1* | 9/2010 | Aranyi ............. A61B 17/07207 227/176.1 |
| 2010/0264195 A1* | 10/2010 | Bettuchi ............. A61B 17/115 227/181.1 |
| 2010/0331859 A1 | 12/2010 | Omori |
| 2010/0331880 A1 | 12/2010 | Stopek |
| 2011/0034910 A1 | 2/2011 | Ross et al. |
| 2011/0087279 A1* | 4/2011 | Shah ................ A61B 17/07207 606/219 |
| 2011/0089220 A1 | 4/2011 | Ingmanson et al. |
| 2011/0101070 A1 | 5/2011 | Bettuchi et al. |
| 2011/0125138 A1 | 5/2011 | Malinouskas et al. |
| 2011/0166673 A1 | 7/2011 | Patel et al. |
| 2011/0233259 A1 | 9/2011 | Olson |
| 2011/0278346 A1* | 11/2011 | Hull ................ A61B 17/00491 227/180.1 |
| 2011/0278347 A1 | 11/2011 | Olson et al. |
| 2011/0293690 A1 | 12/2011 | Griffin et al. |
| 2012/0080336 A1* | 4/2012 | Shelton, IV ........... A61B 90/92 206/339 |
| 2012/0083723 A1 | 4/2012 | Vitaris et al. |
| 2012/0145767 A1 | 6/2012 | Shah et al. |
| 2012/0197272 A1 | 8/2012 | Oray et al. |
| 2012/0241491 A1 | 9/2012 | Aldridge et al. |
| 2012/0241492 A1* | 9/2012 | Shelton, IV ......... H05K 999/99 227/175.1 |
| 2012/0241493 A1 | 9/2012 | Baxter, III et al. |
| 2012/0241497 A1* | 9/2012 | Mandakolathur Vasudevan ........ A61B 17/00491 227/176.1 |
| 2012/0253298 A1 | 10/2012 | Henderson et al. |
| 2012/0273547 A1* | 11/2012 | Hodgkinson ........ A61B 17/068 227/176.1 |
| 2013/0105548 A1* | 5/2013 | Hodgkinson .... A61B 17/07292 227/176.1 |
| 2013/0146642 A1* | 6/2013 | Shelton, IV ......... A61B 17/068 227/177.1 |
| 2013/0153635 A1* | 6/2013 | Hodgkinson .... A61B 17/07207 227/176.1 |
| 2013/0153636 A1 | 6/2013 | Shelton, IV et al. |
| 2013/0153638 A1* | 6/2013 | Carter ................ A61B 17/1155 227/179.1 |
| 2013/0153641 A1 | 6/2013 | Shelton, IV et al. |
| 2013/0209659 A1 | 8/2013 | Racenet et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1* | 8/2016 | Casasanta ........ A61B 17/07292 |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |

(56) References Cited

U.S. PATENT DOCUMENTS

| | | | |
|---|---|---|---|
| 2017/0150967 | A1 | 6/2017 | Hodgkinson et al. |
| 2017/0172575 | A1 | 6/2017 | Hodgkinson |
| 2017/0231629 | A1 | 8/2017 | Stopek et al. |
| 2017/0238931 | A1 | 8/2017 | Prescott et al. |
| 2017/0281328 | A1 | 10/2017 | Hodgkinson et al. |
| 2017/0296188 | A1 | 10/2017 | Ingmanson et al. |
| 2017/0354415 | A1 | 12/2017 | Casasanta, Jr. et al. |
| 2018/0125491 | A1 | 5/2018 | Aranyi |
| 2018/0140301 | A1 | 5/2018 | Milliman |
| 2018/0168654 | A1 | 6/2018 | Hodgkinson et al. |
| 2018/0214147 | A1 | 8/2018 | Merchant et al. |
| 2018/0229054 | A1 | 8/2018 | Racenet et al. |
| 2018/0250000 | A1 | 9/2018 | Hodgkinson et al. |
| 2018/0256164 | A1 | 9/2018 | Aranyi |
| 2018/0296214 | A1 | 10/2018 | Hodgkinson et al. |
| 2018/0310937 | A1 | 11/2018 | (Prommersberger) Stopek et al. |
| 2019/0021734 | A1 | 1/2019 | Hodgkinson |
| 2019/0059878 | A1 | 2/2019 | (Tarinelli) Racenet et al. |
| 2019/0083087 | A1 | 3/2019 | Viola et al. |

FOREIGN PATENT DOCUMENTS

| | | | |
|---|---|---|---|
| CN | 101332110 | A | 12/2008 |
| DE | 1602563 | U | 3/1950 |
| DE | 19924311 | A1 | 11/2000 |
| EP | 0327022 | A2 | 8/1989 |
| EP | 0594148 | A1 | 4/1994 |
| EP | 2039308 | A2 | 3/2009 |
| EP | 2090252 | A2 | 8/2009 |
| EP | 2163211 | A2 | 3/2010 |
| EP | 2189121 | A1 | 5/2010 |
| EP | 2258282 | A2 | 12/2010 |
| EP | 2292276 | A2 | 3/2011 |
| EP | 2491867 | A1 | 8/2012 |
| EP | 2497431 | A1 | 9/2012 |
| EP | 2620105 | A1 | 7/2013 |
| EP | 2762091 | A2 | 8/2014 |
| JP | 2000166933 | A | 6/2000 |
| JP | 2002202213 | A | 7/2002 |
| JP | 2003000603 | A | 1/2003 |
| JP | 2003190178 | A | 7/2003 |
| JP | 2007124166 | A | 5/2007 |
| JP | 2008289883 | A | 12/2008 |
| JP | 2008307393 | A | 12/2008 |
| JP | 2009189847 | A | 8/2009 |
| JP | 2010142636 | A | 7/2010 |
| JP | 2010214132 | A | 9/2010 |
| WO | 90/05489 | A1 | 5/1990 |
| WO | 95/16221 | A1 | 6/1995 |
| WO | 98/38923 | A1 | 9/1998 |
| WO | 9926826 | A2 | 6/1999 |
| WO | 0010456 | A1 | 3/2000 |
| WO | 0016684 | A1 | 3/2000 |
| WO | 2005079675 | A2 | 9/2005 |
| WO | 2008109125 | A1 | 9/2008 |
| WO | 2010/075298 | A2 | 7/2010 |

OTHER PUBLICATIONS

Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
Extended European Search Report corresponding to EP 16 15 3647.9 dated Jun. 3, 2016.
Extended Office Action corresponding to counterpart Int'l Appln. No. EP 13 18 0881.8 dated Nov. 18, 2016.
European Office Action corresponding to EP 14 17 2681.0 dated May 13, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Australian Examination Report No. 1 corresponding to AU 2013211499 dated May 4, 2017.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2014201008 dated May 23, 2017.
Japanese Office Action corresponding to counterpart Int'l Appln. No. JP 2013-169083 dated May 31, 2017.

(56) References Cited

OTHER PUBLICATIONS

European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Canadian Office Action dated Jul. 16, 2019 corresponding to counterpart Patent Application CA 2,823,283.
Japanese Office Action corresponding to JP 2013-250857 dated Aug. 17, 2017.
Japanese Office Action corresponding to JP 2013-229471 dated Aug. 17, 2017.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).

(56) References Cited

OTHER PUBLICATIONS

Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 13 180 881.8 dated Jun. 19, 2015; 4 pp.
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Canadian Office Action corresponding to CA 2,665,206 dated Nov. 19, 2013.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.

\* cited by examiner

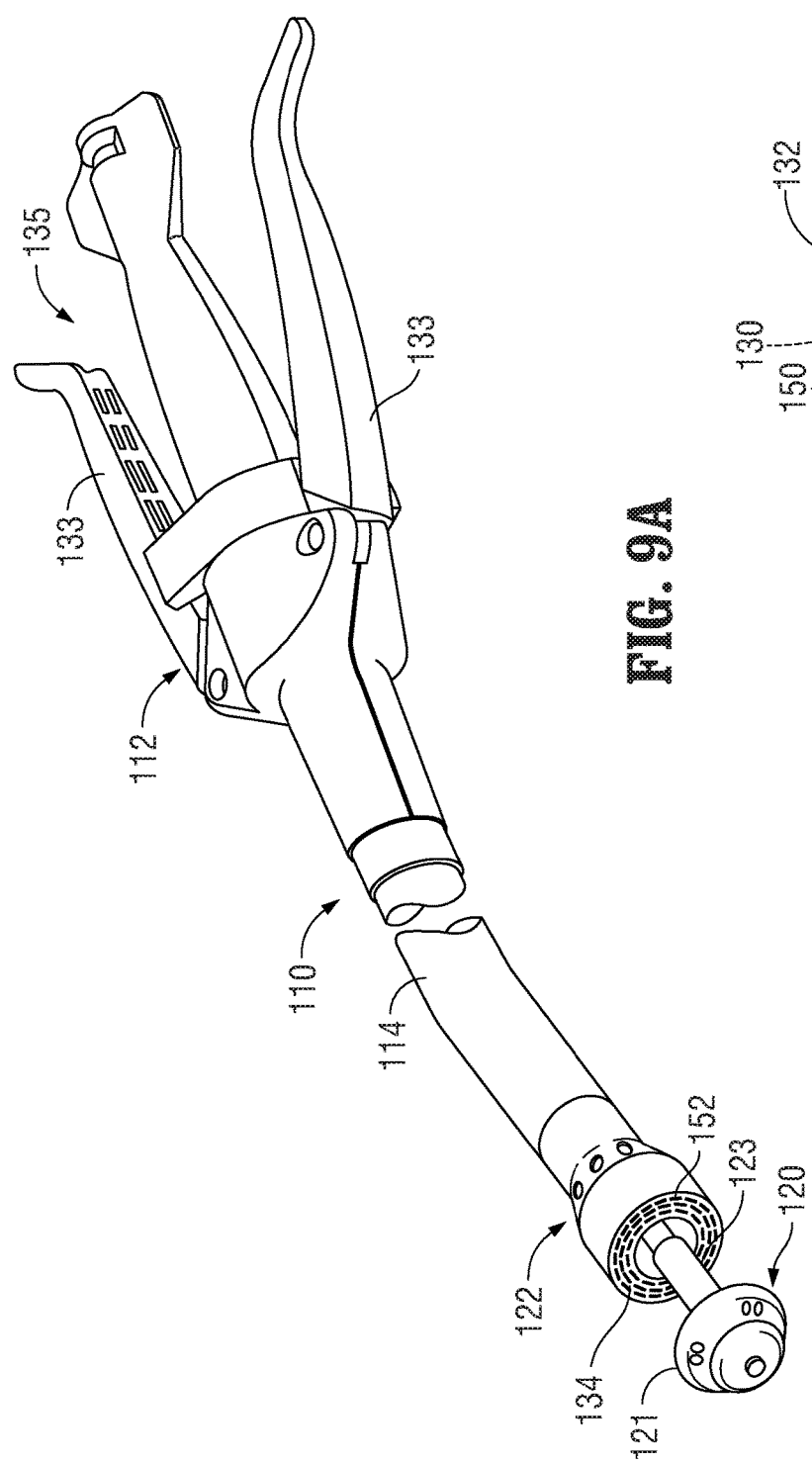
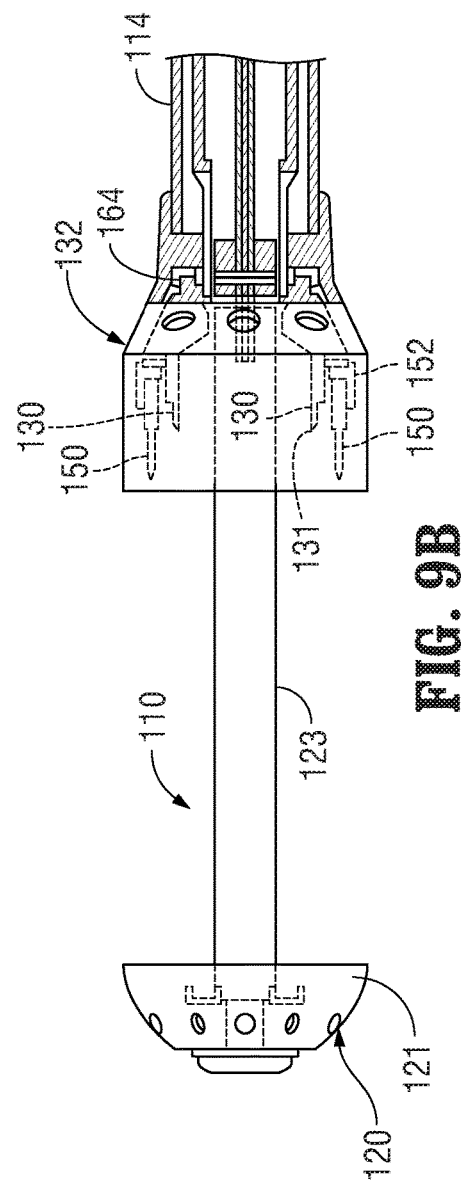
FIG. 9A
FIG. 9B

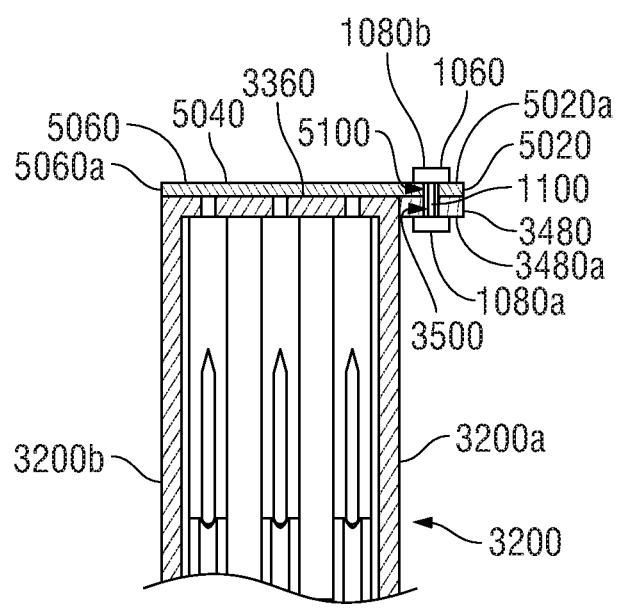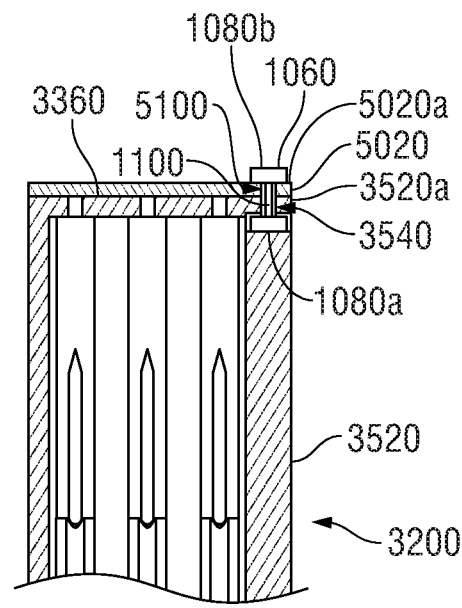
FIG. 20A   FIG. 20B
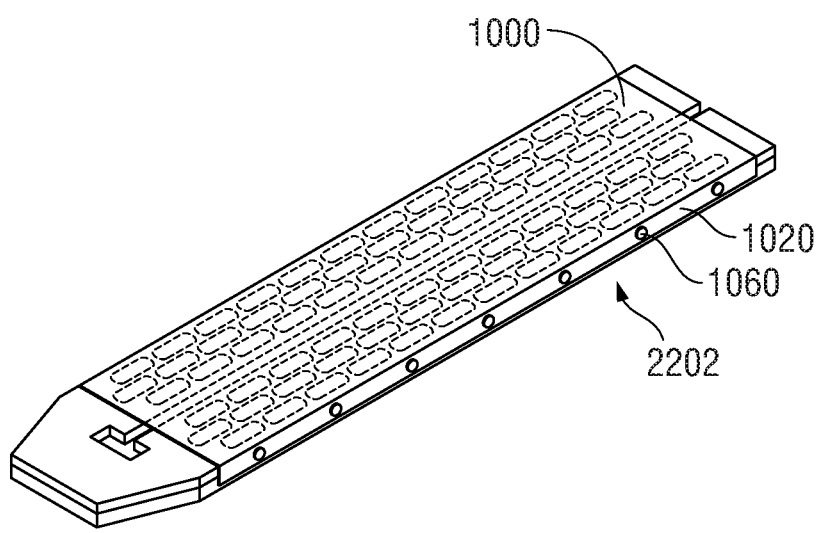
FIG. 21

BUTTRESS ATTACHMENT FEATURES FOR SURGICAL STAPLING APPARATUS

CROSS-REFERENCE TO RELATED APPLICATION

This application is a continuation application of U.S. patent application Ser. No. 13/942,822, filed on Jul. 16, 2013, which claims the benefit of and priority to U.S. Provisional Patent Application Ser. No. 61/684,846 filed on Aug. 20, 2012, the entire content of each of which is incorporated by reference herein.

BACKGROUND

1. Technical Field

The present disclosure relates to surgical stapling apparatuses and buttress materials for use with said surgical stapling apparatus and, more particularly, to structures and methods for attaching a buttress material to a surgical stapling apparatus.

2. Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the stapling apparatus is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the apparatus to cut the tissue between the lines of staples.

For most procedures, the use of bare staples, with the staples in direct contact with the patient's tissue, is generally acceptable. In certain procedures, the use of surgical supports, e.g., meshes or buttress materials, are employed by surgeons in combination with linear or annular stapling devices to bridge, repair and/or reinforce tissue defects within a patient, especially those occurring in the abdominal wall, chest wall, diaphragm, and other musculo-aponeurotic areas of the body. The buttress material tends to reinforce the staple or suture line as well as cover the juncture of the tissues to reduce leakage prior to healing. In certain minimally invasive surgical procedures the buttress material may be pre-attached to the surgical instrument being used. For example, the buttress material can be attached to a staple cartridge or anvil plate of a surgical stapling instrument by the manufacturer.

A surgical stapling apparatus having a surgical buttress releasably secured thereto by at least one anchor is disclosed in International Published Application No. WO 08/109125 A1, the disclosure of which is hereby incorporated by reference herein in its entirety. The buttress is attached to the apparatus by at least one anchor and includes knife blades for severing the anchors.

U.S. Pat. No. 5,441,193 to Gravener, the disclosure of which is hereby incorporated by reference herein in its entirety, discloses a surgical device having a sheet of curved resilient material attached thereto. Elongated projections can be fixed within slots using adhesive bonding and perforations permit tearing of the film to separate the central portion of the film from the side portions.

It would be desirable to provide improved means of securely attaching a surgical buttress to the staple cartridge or anvil plate while allowing the buttress material to fully release from the surgical stapling apparatus after the staples have been fired.

SUMMARY

Disclosed herein is a surgical stapling apparatus including a buttress material and a method of attaching the buttress material to the surgical stapling apparatus.

In one embodiment of present application a system for securing surgical buttresses to the jaws of the stapler is disclosed. The system allows the surgical buttresses to be secured to the staple cartridge and/or anvil plate by utilizing ultraviolet light curable epoxy to adhere the surgical buttresses to a tissue contacting surface of the staple cartridge and/or anvil plate. Perforations may be provided around the location of the epoxy to allow the surgical buttress to release from the tissue contacting surfaces by the force applied by the grasp of staples in the surgical buttress.

In accordance with one embodiment of the present disclosure, the use of ultraviolet light curable epoxy allows the same attachment means to be utilized for both the metal based anvil plate and metal or non-metal staple cartridge. In addition, the use of ultraviolet light curable epoxy can be precisely controlled both in terms of spatial placement and volume of deposition as to not impact the anvil plate or staple cartridge. Most importantly, the ultraviolet light curable epoxy is essentially part of the stapling device as it does not detach with the surgical material and is not implanted into the body.

In another embodiment of the present disclosure, surgical buttresses are secured to the staple cartridge and/or anvil plate with the use of retaining members placed through at least one hole of the surgical buttress and through at least one opening of at least one of the staple cartridge and/or anvil plate.

In one aspect of the present disclosure, a staple cartridge for use with a surgical stapling apparatus is disclosed. The staple cartridge includes a cartridge body including a tissue contacting surface defining a plurality of staple retaining slots. The tissue contacting surface of the cartridge body is fabricated from a first material. The staple cartridge further includes a staple disposed within each staple retaining slot of the cartridge body. A buttress material is releasably disposed on the tissue contacting surface of the cartridge body and an epoxy is positioned on the tissue contacting surface of the cartridge body defining an attachment zone configured to retain the buttress material atop the tissue contacting surface.

In an aspect of the present disclosure, the epoxy is an ultraviolet light curable epoxy.

In an aspect of the present disclosure, the tissue contacting surface has a first and second outer edge.

In an aspect of the present disclosure, the tissue contacting surface has a distal end such that a distal attachment zone is positioned from the first outer edge to the second outer edge.

In an aspect of the present disclosure, the tissue contacting surface has a proximal end such that a first proximal attachment zone is positioned parallel to the first outer edge and second proximal attachment zone is positioned parallel to the second outer edge.

In an aspect of the present disclosure, the staple cartridge defines a central longitudinal slot configured to enable passage of a knife blade therethrough.

In an aspect of the present disclosure, the first and second proximal attachment zones are positioned distally from a proximal end of the central longitudinal slot.

In an aspect of the present disclosure, the distal attachment zone is positioned proximally for a distal end of the central longitudinal slot.

In an aspect of the present disclosure, the buttress material has perforations at the proximal end of the tissue contacting surface such that the perforations are positioned perpendicularly and distally from the first and second proximal attachment zone.

In an aspect of the present disclosure, the buttress material has perforations at the distal end of the tissue contacting surface such that the perforations are positioned parallel and proximal from the at least one distal attachment zone.

In an aspect of the present disclosure, a plurality of attachment zones are disposed intermittently along the first and second outer edges.

In an aspect of the present disclosure, the plurality of attachment zones are concentric.

In an aspect of the present disclosure, the buttress material has perforations such that the perforations surround the plurality of attachment zones.

In an aspect of the present disclosure, an end effector assembly for a surgical stapler is disclosed. The end effector including a staple cartridge having a tissue contacting surface, the tissue contacting surface of the cartridge body being fabricated from a first material. The end effector further including an anvil plate having a tissue contacting surface, the tissue contacting surface of the anvil plate being fabricated from a second material that is dissimilar from the first material. A buttress material is releasably disposed on the tissue contacting surfaces of each of the staple cartridge and the anvil plate and an epoxy positioned onto the tissue contacting surfaces of each of the staple cartridge and anvil plate defining an attachment zone configured to retain the respective buttress material atop the respective tissue contacting surfaces.

In an aspect of the present disclosure, a surgical stapling apparatus is disclosed. The apparatus includes a cartridge body including a tissue contacting surface defining a plurality of staple retaining slots and a staple disposed with each staple retaining slot of the cartridge body. The staple cartridge further includes a substantially circular buttress material releasably disposed on the tissue contacting surface of the cartridge body, the buttress material including an inner peripheral edge, an outer peripheral edge, and a middle portion extending between the inner and outer peripheral edges and an epoxy positioned on the tissue contacting surface of the cartridge body defining an attachment zone configured to retain the buttress material atop the tissue contacting surface. In certain preferred embodiments, the epoxy is a curable epoxy, and may be curable upon exposure to ultraviolet light.

The buttress material may further include perforations arranged to allow the buttress material to separate from the cartridge body. A retaining member may also be disposed in a hole in the surgical stapling apparatus.

In a further aspect of the present disclosure, a method of assembling a surgical stapling apparatus comprises: providing a surgical stapling apparatus having at least one tissue contacting surface, the tissue contacting surface having a stapling zone and at least one attachment zone; applying epoxy on the at least one attachment zone on the tissue contacting surface; applying a buttress to the tissue contacting surface so as to contact at least a portion of the buttress with the epoxy, the buttress having a portion for overlying the stapling zone and a portion overlying the attachment zone for being permanently attached to the tissue contacting surface; and curing the epoxy.

The epoxy may be curable with exposure to ultraviolet light. In certain embodiments, the surgical stapling apparatus has an anvil plate and a staple cartridge. The surgical stapling apparatus can be selected from the group consisting of a circular surgical stapler and a linear surgical stapler. The method can include disposing a retaining member in a hole in the surgical stapling apparatus.

Any of the above aspects of the present disclosure described may be combined with any other aspect of the present disclosure without departing from the scope of the present disclosure.

In another aspect of the present disclosure, a tool assembly for use in a surgical stapling apparatus for joining tissue portions is disclosed. The tool assembly includes a staple cartridge containing a plurality of surgical staples therein and an anvil plate configured to cooperate with the staple cartridge to grasp tissue disposed therebetween where at least one of the staple cartridge and the anvil plate includes at least one opening. The tool assembly further includes a buttress material supported on the at least one of the staple cartridge and the anvil plate and including at least one hole formed therein. The tool assembly further includes at least one retaining member extending through the at least one hole and the at least one opening. The retaining member is configured to releasably secure the buttress material to the at least one of the staple cartridge and the anvil plate and is configured to separate from the buttress material to release the buttress material from the at least one of the staple cartridge and the anvil plate after firing of the surgical stapling apparatus.

In an aspect of the present disclosure, the at least one retaining member includes a pair of buttons and a tether extending therebetween. The tether extends through the at least one hole and the at least one opening with one of the buttons disposed adjacent each of the at least one hole and the at least one opening to releasably secure the buttress material to the at least one of the staple cartridge and the anvil plate.

In an aspect of the present disclosure, the pair of buttons are sized such that a diameter of each button is larger than the respective hole or opening.

In an aspect of the present disclosure, the at least one of the staple cartridge and the anvil plate includes a tissue contacting surface and a side surface. The buttress material includes a flap extending beyond the tissue contacting surface and configured for placement adjacent the side surface. The flap includes the at least one hole extending therethrough and the at least one opening is disposed in the side surface such that the at least one retaining member releasably secures the flap to the side surface.

In an aspect of the present disclosure, the surgical stapling apparatus is a linear surgical stapling apparatus.

In an aspect of the present disclosure, the at least one hole includes a plurality of holes longitudinally spaced along the buttress material.

In an aspect of the present disclosure, the at least one hole includes a plurality of holes spaced along the buttress material transverse to a longitudinal axis of the tool assembly.

In an aspect of the present disclosure, the at least one hole is disposed adjacent to a corner of the buttress material and the at least one opening extends through a tissue contacting surface of the at least one of the staple cartridge and the anvil plate.

In an aspect of the present disclosure, the surgical stapling apparatus is a circular surgical stapling apparatus.

In an aspect of the present disclosure, the at least one hole includes a plurality of holes annularly spaced along the buttress material.

In an aspect of the present disclosure, the buttress material includes a first flap adjacent an inner side surface of the at least one of the staple cartridge and the anvil plate and a second flap adjacent an outer surface of the at least one of the staple cartridge and the anvil plate. Each of the first and second flaps includes the at least one hole and each of the inner and outer side surfaces includes the at least one opening.

In an aspect of the present disclosure, a tissue contacting surface of the at least one of the staple cartridge and the anvil plate includes a flange extending radially inward therefrom. The buttress material is supported on the flange and includes the at least one hole adjacent the flange. The flange includes the at least one opening therein.

In an aspect of the present disclosure, the retaining member is formed of a bioabsorbable polymer.

In an aspect of the present disclosure, the retaining member is configured to fracture after the plurality of surgical fasteners are fired.

In an aspect of the present disclosure, the retaining member is dissolvable in a body fluid.

In an aspect of the present disclosure, the retaining member dissolvable in saline.

In an aspect of the present disclosure, the retaining member has a melt temperature of about body temperature.

In an aspect of the present disclosure, retaining member has a melt temperature of about 37° C.

In an aspect of the present disclosure, the buttress material includes a plurality of perforations that are configured to allow the retaining member to separate from the buttress material.

In yet another aspect of the present disclosure, a method of attaching a buttress material to a surgical stapling apparatus during assembly is disclosed. The method includes the steps of: providing a staple cartridge containing a plurality of surgical staples therein, providing an anvil plate configured to cooperate with the staple cartridge to grasp tissue disposed therebetween, positioning a buttress material on at least one of the staple cartridge and the anvil plate, inserting a retaining member having a first end and a second end through at least one hole of the buttress material and at least one opening of the at least one of the staple cartridge and the anvil plate, and melting the retaining member to form a button on each of the first and second ends to releasably secure the buttress material to the at least one of the staple cartridge and the anvil plate.

In an aspect of the present disclosure, the buttons are formed such that a diameter of each button is larger than the respective hole or opening.

In an aspect of the present disclosure, a surgical stapling apparatus for joining tissue portions is disclosed. The apparatus includes a staple cartridge having a plurality of surgical staples disposed therein and at least one opening formed therein. The staple cartridge further includes a buttress material supported on the staple cartridge and including at least one hole formed therein and at least one retaining member extending through the at least one hole and the at least one opening. The retaining member is configured to releasably secure the buttress material to the staple cartridge and is configured to separate from the buttress material to release the buttress material from the staple cartridge after firing of the surgical stapling apparatus.

BRIEF DESCRIPTION OF THE DRAWINGS

Various embodiments of the presently disclosed interlocking buttress retention systems are disclosed herein with reference to the drawings, wherein:

FIG. 9A is a perspective view of an illustrative embodiment of a surgical stapling apparatus in accordance with another embodiment of the present disclosure;

FIG. 9B is a side elevational view partially, broken away, of the surgical stapling apparatus of FIG. 9A;

FIG. 20A is a side, cross-sectional view of the staple cartridge of FIG. 19A, taken along section line 20A-20A of FIG. 19A, illustrating the staple cartridge having a flange;

FIG. 20B is a side, cross-sectional view of another embodiment of a staple cartridge of FIG. 19A, illustrating the staple cartridge having a relatively wider inner surface;

FIG. 21 is a perspective view of a anvil plate of the surgical stapling apparatus of FIG. 1, illustrating a buttress material supported thereon in accordance with another embodiment of the present disclosure.

DETAILED DESCRIPTION OF THE EMBODIMENTS

Figure 1:
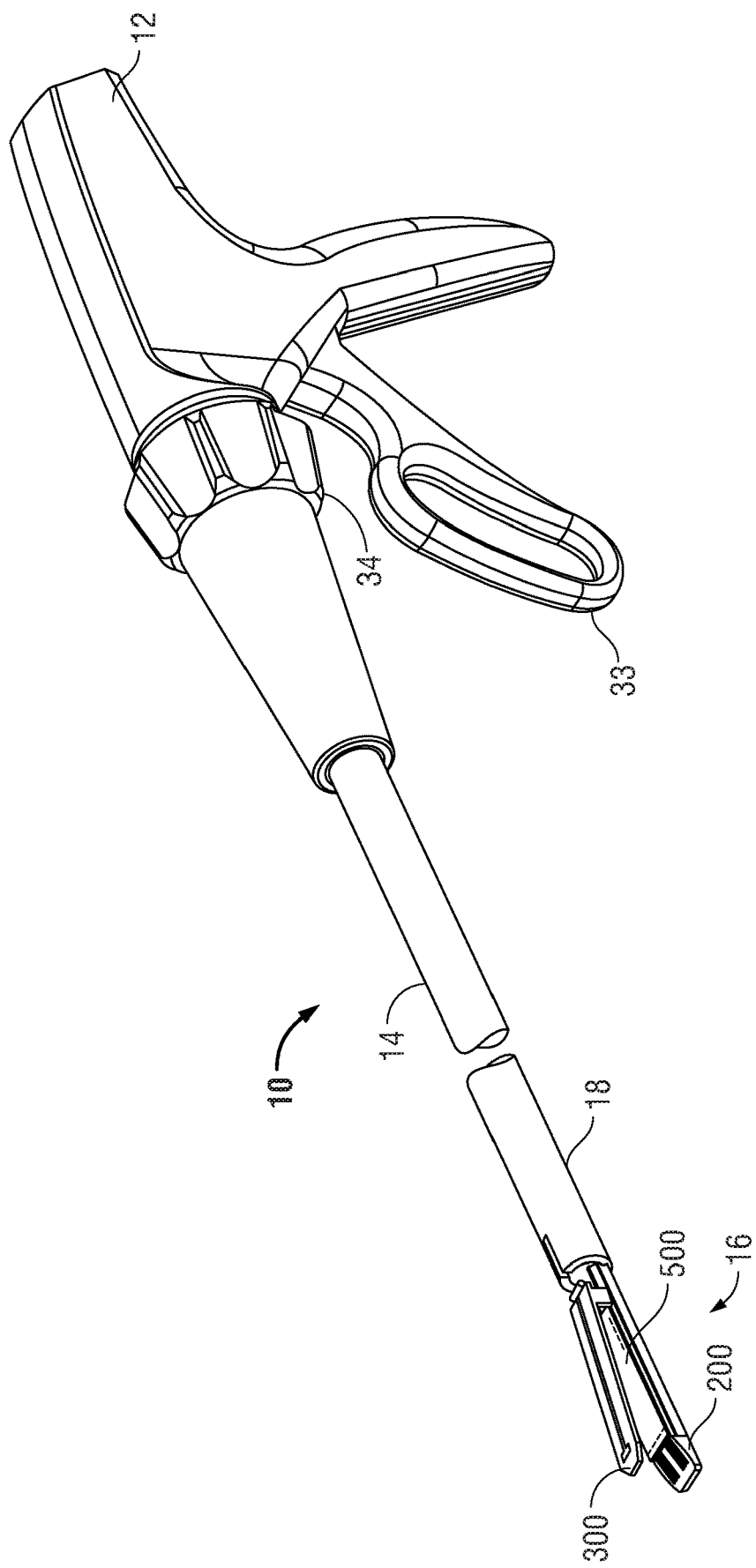
FIG. 1 is a perspective view of a surgical stapling apparatus according to an embodiment of the present disclosure.

Various exemplary embodiments of the present disclosure are discussed herein below in terms of buttresses for use with surgical stapling apparatus. The buttresses described herein may be used in sealing a wound by approximating the edges of wound tissue between a staple cartridge and an anvil plate of a surgical stapling apparatus which contains at least one buttress. The at least one buttress is joined to the surgical stapling apparatus by at least one attachment zone formed by an epoxy positioned between a tissue contacting surface of each of the staple cartridge and anvil plate and the least one buttress. Firing of the surgical stapling apparatus forces legs of at least one staple to pass through an opening on the staple cartridge, the tissue, and the openings on the anvil plate to secure the buttress to the tissue, to secure the adjoining tissue to one another, and to seal the tissue. Thus, the present disclosure describes surgical buttresses, surgical stapling apparatus supporting said surgical buttresses, and methods and mechanisms for using the same.

It should be understood that a variety of surgical stapling apparatus may be utilized with a surgical buttress of the present disclosure. For example, linear stapler configurations may be utilized, such as, for example those including Duet TRS' reloads and staplers with Tri-Staple™ technology, available through Covidien, which maintain a principal place of business at 555 Long Wharf Drive, North Haven, Conn. 06511, and transverse anastomosis staplers, such as, for example, EEA™, CEEA™, GIA™, EndoGIA™, and TA™ surgical staplers, also available through Covidien. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference); laparoscopic staplers (see, e.g., commonly owned U.S. Pat. Nos. 6,330,965 and 6,241,139, each entitled "Surgical Stapling Apparatus," the entire contents of each of which being incorporated herein by this reference); and transverse anastomosis staplers (see, e.g., commonly owned U.S. Pat. Nos. 5,964,394 and 7,334,717, each entitled "Surgical Fastener Applying Apparatus", the entire contents of each of which being incorporated herein by this reference).

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to FIG. 1, there is disclosed an exemplary surgical stapling apparatus or surgical stapler 10 for use in stapling tissue and applying a buttress material or surgical buttress to the tissue. An exemplary example of this type of surgical stapling instrument is disclosed in U.S. Pat. No. 7,128,253, the entire disclosure of which is incorporated by reference herein.

Surgical stapling apparatus 10 generally includes a handle 12 having an elongate tubular member 14 extending distally from handle 12. An end effector assembly 16 is mounted on a distal end 18 of elongate tubular member 14. End effector assembly 16 includes a staple cartridge 200 configured to receive a cartridge body 32 therein and an anvil plate 300. End effector assembly 16 may be permanently affixed to elongate tubular member 14 or may be detachable and thus replaceable with a new end effector assembly 16. Anvil plate 300 is movably mounted on distal end 18 of jaw assembly 16 and is movable between an open position spaced apart from staple cartridge 200 to a closed position substantially adjacent staple cartridge 200. Anvil plate 300 is fabricated from a metal material, including and not limited to stainless steel, titanium, titanium alloy, and the like. At least a tissue contacting surface of staple cartridge 200 is fabricated from a material other than metal, including and not limited to plastic, thermoplastic, resin, polycarbonate, and the like.

Surgical stapling apparatus 10 further includes a trigger 33, as seen in FIG. 1, movably mounted on handle 12. Actuation of trigger 33 initially operates to move anvil plate 300 from the open to the closed position relative to staple cartridge 200 and subsequently actuates surgical stapling apparatus 10 to apply lines of staples to tissue. In order to properly orient end effector assembly 16 relative to the tissue to be stapled, surgical stapling apparatus 10 is additionally provided with a rotation knob 34 mounted on handle 12. Rotation of rotation knob 34 relative to handle 12 rotates elongate tubular member 14 and end effector assembly 16 relative to handle 12 so as to properly orient end effector assembly 16 relative to the tissue to be stapled.

Figure 6:
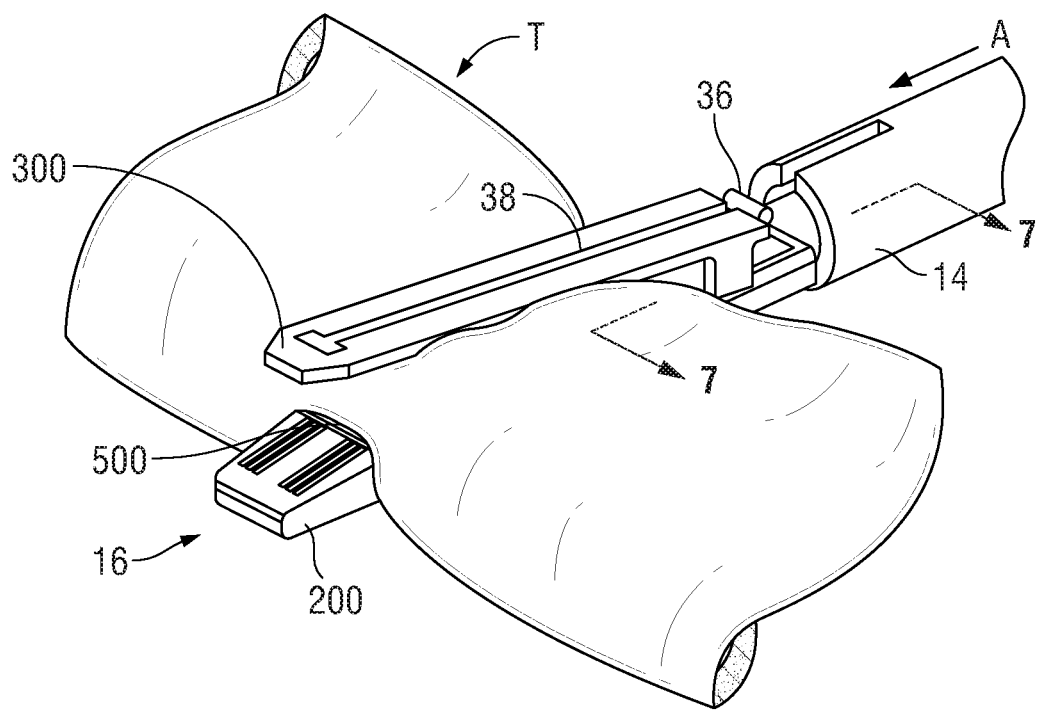
FIG. 6 is a perspective view of a distal end of the surgical stapling apparatus of FIG. 1, shown in use positioned about a tissue section.

A driver 36, as seen in FIGS. 6 and 7A, is provided to move anvil plate 300 between the open and closed positions relative to staple cartridge 200. Driver 36 moves through a longitudinal slot 338 (FIG. 3) formed in anvil plate 300. A knife 30 with knife blade 31 is associated with driver 36 to cut tissue captured between staple cartridge 200 and anvil plate 300 as driver 36 passes through slot 338. The driver may be configured as a beam with an upper portion that engages the anvil plate 300 and a lower portion that engages the channel that supports the staple cartridge 200. For example, U.S. Pat. No. 7,565,993 to Milliman et al., the disclosure of which is hereby incorporated by reference herein in its entirety, discloses an axial drive assembly 212 including an elongated drive beam 266 for approximating the anvil and staple cartridge to clamp tissue and fire staples therein. The stapling apparatus 10 can include such a beam, or other known structure. The staple cartridge 200 has staple receiving slots for retaining staples therein, whereas the anvil plate includes staple forming recesses. The driver forces the staples from the staple receiving slots and drives them into the staple forming recesses so that they are formed into a closed shape around tissue.

Reference may be made to commonly owned U.S. Pat. Nos. 5,915,616, 6,330,965, and 6,241,139, referenced above, for a detailed discussion of the construction and operation of an exemplary surgical stapling apparatus 10.

Staple cartridge 200 and/or anvil plate 300 may be provided with a surgical buttress 500. Surgical buttress 500 is provided to reinforce and seal the lines of staples applied to tissue by surgical stapling apparatus 10. Surgical buttress 500 may be configured into any shape, size, or dimension suitable to fit any surgical stapling, fastening, or firing apparatus.

Staple cartridge 200 is provided with a cartridge buttress 500a and anvil plate 300 is provided with an anvil buttress 500b in the manners described in more detail hereinbelow. The buttresses 500a, 500b may be made from any biocompatible natural or synthetic material. The material from which the buttresses 500a, 500b are formed may be bioabsorbable or non-bioabsorbable. It should be understood that any combination of natural, synthetic, bioabsorbable and non-bioabsorbable materials may be used to form the buttress material. The buttresses 500a, 500b may be porous or non-porous, combination of porous and non-porous layers. The non-porous buttresses 500a, 500b may be utilized to retard or prevent tissue ingrowth from surrounding tissues thereby acting as an adhesion barrier and preventing the formation of unwanted scar tissue.

Additional exemplary materials for surgical buttresses 500a, 500b for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of being hereby incorporated herein by reference in their entirety.

As illustrated in the current embodiment and shown in FIGS. 2 and 3, surgical buttress 500 is releasably attached to staple cartridge 200 and/or anvil plate 300 at attachment zones 240, 340, respectively, defined by strategically positioned ultraviolet (UV) light curable epoxy that affixes surgical buttresses 500a, 500b to the inwardly facing or tissue contacting surfaces 220, 320 of the staple cartridge 200 and/or the anvil plate 300, as discussed in detail below. The use of UV curably epoxy enables fixing of surgical buttresses 500a, 500b to the respective tissue contacting surfaces 220, 320 of staple cartridge 200 and anvil plate 300 which are fabricated from dissimilar material.

Figure 2:
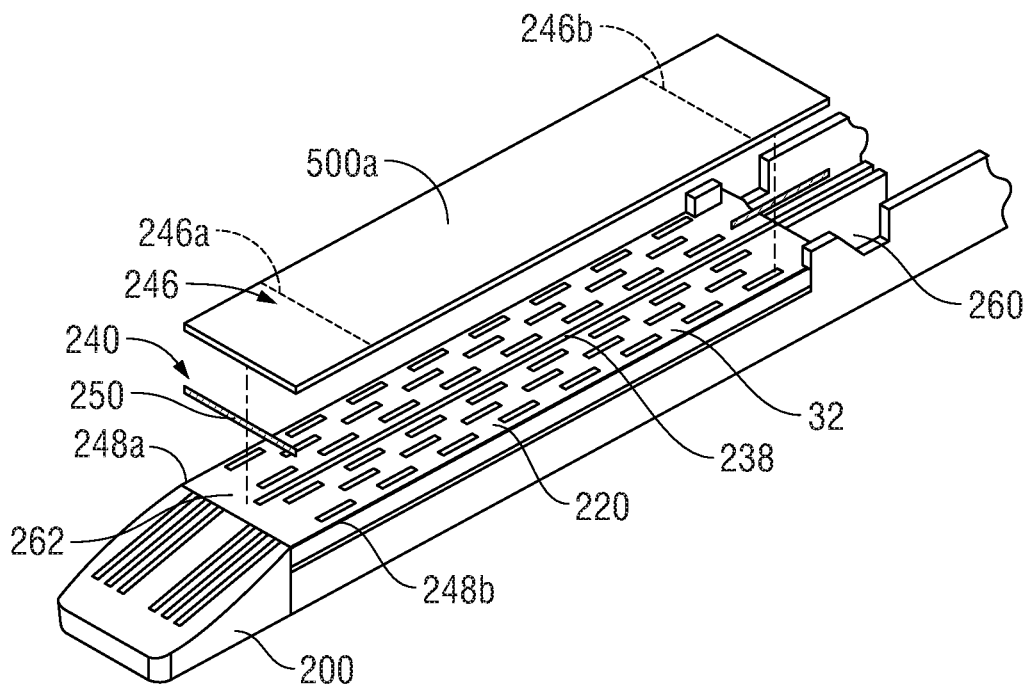
FIG. 2 is a perspective view, with parts separated, of a staple cartridge of the surgical stapling apparatus of FIG. 1, illustrating a surgical buttress associated therewith.

With reference to FIG. 2, cartridge buttress 500a of staple cartridge 200 is operatively secured or adhered to a tissue contacting surface 220 of staple cartridge 200, by epoxy 250 positioned onto both a proximal end 260 and a distal end 262 of the tissue contacting surface 220. Epoxy 250 is disposed between the cartridge buttress 500a and the tissue contacting surface 220. Staple cartridge 200 further includes a first outer edge 248a and second outer edge 248b. A distal attachment zone 240a (FIG. 4) is disposed distally of a distal end of a central longitudinal slot 238 and extends substantially from the first outer edge 248a to the second outer edge 248b of staple cartridge 200. At least one proximal attachment zone 240b is disposed proximally of the distal end of the central longitudinal slot 238. The proximal and distal attachment zones on the staple cartridge are positioned outside the area in which the staple receiving slots are defined in the staple cartridge.

Cartridge buttress 500a includes perforations 246 that allow cartridge buttress 500a to be released from the tissue contacting surface 220. Perforations 246 extend linearly in a direction perpendicular to the central longitudinal slot 238 near the proximal and distal attachment zones 240a, 240b. In particular, at the distal end 262 of staple cartridge 200, perforations 246a of the cartridge buttress 500a are disposed between the distal attachment zone 240a and the distal end of the central longitudinal slot 238. Further, at the proximal end 260 of staple cartridge 200, the perforations 246b of the cartridge buttress 500a are disposed distally of each proximal attachment zone 240b.

Figure 3:
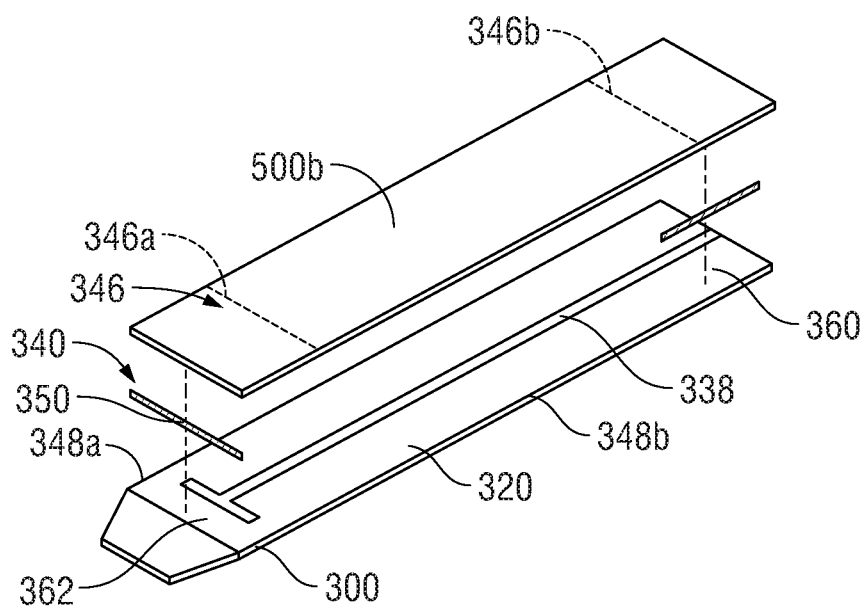
FIG. 3 is a perspective view, with parts separated, of an anvil plate of the surgical stapling apparatus of FIG. 1, illustrating a surgical buttress associated therewith.

With reference to FIG. 3, and similar to cartridge buttress 500a, anvil buttress 500b is operatively secured or adhered to a tissue contacting surface 320 of anvil plate 300, by epoxy 350 positioned at a proximal 360 and distal end 362 of the anvil plate 300 and between the anvil buttress 500b and the tissue contacting surface 320 of anvil plate 300. A distal attachment zone 340a (FIG. 5) is disposed distally of a distal end of a central longitudinal slot 338 and extends substantially between the outer edges 348a, 348b of anvil plate 300. At least one proximal attachment zone 342b is disposed proximally of the distal end of the central longitudinal slot 338. The proximal and distal attachment zones on the anvil plate 300 are positioned outside the area in which the staple receiving recesses are defined in the anvil plate.

Anvil buttress 500b includes perforations 346 similar to cartridge buttress 500a. Perforations 346 of anvil buttress 500b extend linearly in a direction perpendicular to the central longitudinal slot 338 near the proximal and distal attachment zones 340a, 340b from the first and second outer edges 348a, 348b. In particular, at the distal end 362 of anvil plate 300, the perforations 346a of the anvil buttress 500b are disposed between the distal attachment zone 340a and the distal end of the central longitudinal slot 338. Further, at the proximal end 360 of anvil plate 300, the perforations 346b of the anvil buttress 500b are disposed distally of each proximal attachment zone 340b. the perforations enable the buttresses 500a, 500b to be permanently attached to the anvil plate and staple cartridge while allowing the release of the buttresses after stapling has been performed.

Figure 4:
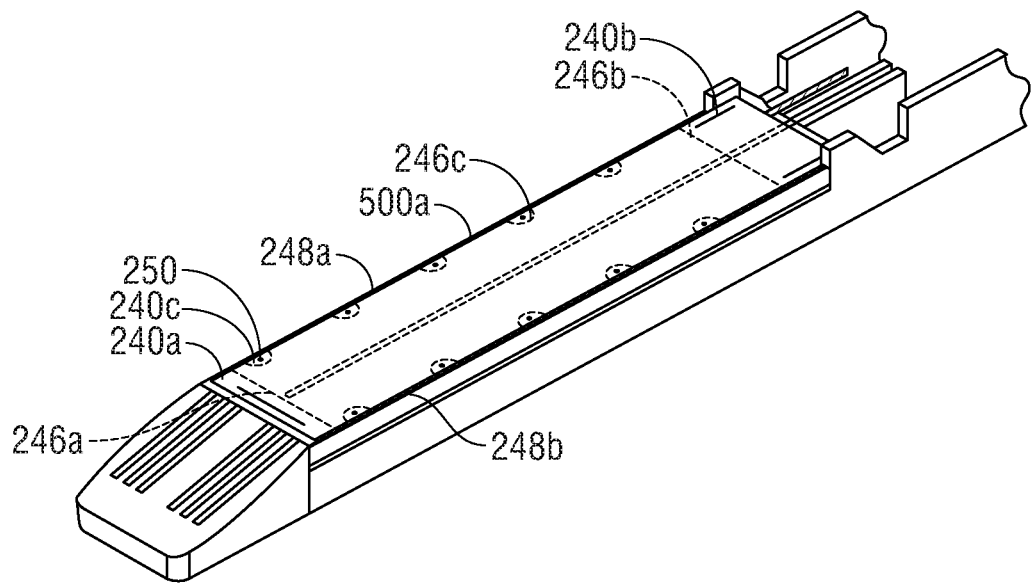
FIG. 4 is a perspective view of the staple cartridge, illustrating the surgical buttress affixed to the staple cartridge.
Figure 5:
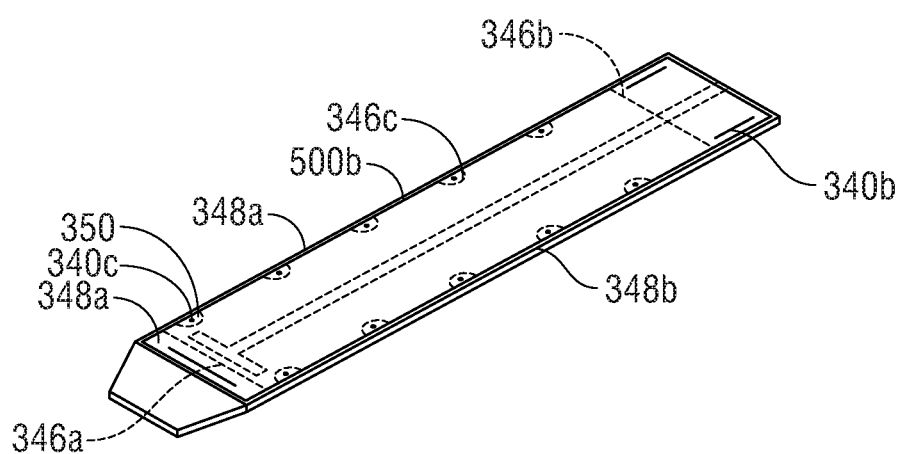
FIG. 5 is a perspective view of the anvil plate, illustrating the surgical buttress affixed to the anvil plate.

FIGS. 4 and 5 illustrate the buttresses 500a, 500b disposed on the staple cartridge 200 and anvil plate 300, respectively. As shown, additional attachment zones 240c, 340c, for respective staple cartridge 200 and anvil plate 300, are disposed along outer edges 248a, 248b, 348a, 348b of each of staple cartridge 200 and anvil plate 300. Perforations 246c, 346c surround the attachments zones 240c, 340c to allow buttresses 500a, 500b to be released from the tissue contacting surfaces 220, 320. The attachment zones 240c, 340c are shown as concentric but additional shapes and sizes may be contemplated. The attachment zones in any of the embodiments disclosed herein may have shapes that are circular, rectangular, oblong, etc., or any appropriate shape. Likewise, the epoxy material in any of the embodiments disclosed herein may have shapes that are circular, rectangular, oblong, etc., or any appropriate shape.

During assembly, epoxy 250, 350 is disposed at predetermined locations on tissue contacting surfaces 220, 320 of each of staple cartridge 200 and anvil plate 300 by known methods, such as spraying, dipping, blotting, dabbing, or similar known methods in the art. Once the buttresses 500a, 500b are placed onto each of the tissue contacting surfaces 220, 320 of staple cartridge 200 and anvil plate 300, respectively, an ultraviolet light is used to cure epoxy 250, 350 and bond buttresses 500a, 500b to the epoxy 250, 350 and thus to the tissue contacting surfaces 220, 320. In any of the embodiments disclosed herein, it is contemplated that the epoxy could be partially cured and then the buttress is adhered to the partially cured epoxy.

In any of the embodiments disclosed herein, the epoxy can be an epoxy that is cured using any electromagnetic radiation, including but not limited to ultraviolet light.

As illustrated in FIG. 6, during use of surgical stapling apparatus 10, the staple cartridge 200 and anvil plate 300, having surgical buttresses 500a, 500b loaded thereon (as described above) are positioned on either side of the surgical site. Tissue contacting surfaces 220, 320 of staple cartridge 200 and anvil plate 300 are positioned adjacent layers of tissue "T" to be fastened to one another.

Figure 7:
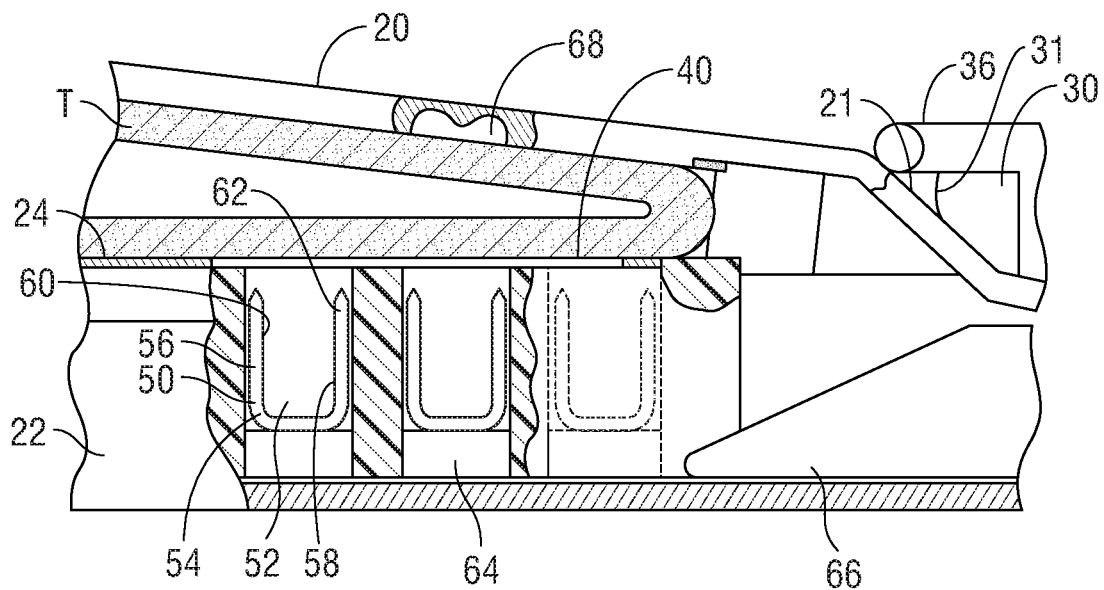
FIG. 7 is a cross-sectional view taken along line 7-7 of FIG. 6.

As shown in FIG. 7, staple cartridge 22 includes surgical staples 50 positioned within the individual staple retaining slots 52. Staples 50 are of a conventional type and include a backspan 54 having a pair of legs 56 and 58 extending from backspan 54. Legs 56 and 58 terminate in tissue penetrating tips 60 and 62, respectively. Pushers 64 are located within staple retaining slots 52 and are positioned between staples 50 and the path of a drive bar 66.

Surgical stapling apparatus 10 is initially actuated by movement of trigger 33 relative to handle 12 (FIG. 1) causing driver 36 to move in the direction of arrow "A" (FIG. 6), and against sloped edge 21 of anvil plate 300 thereby causing anvil plate 300 to be moved to the closed position relative to staple cartridge 200. As drive bar 66 advances distally within staple cartridge 32, drive bar 66 urges pushers 64 upwardly against backspan 54 of staples 50 driving legs 56 and 58 of staples 50 through the cartridge buttresses 500a, tissue "T", and anvil buttress 500b, towards staple forming pockets 68 in anvil plate 300. Tissue penetrating tips 60 and 62 of staple legs 56 and 58 are bent within staple forming pockets 68 in anvil plate 20 with backspan 54 securing surgical buttress 24 against tissue "T". The buttresses 500a, 500b tear along the perforations 246, 346 thereby breaking the bonds formed by the epoxy 250, 350 and releasing the buttresses 500a, 500b from the tissue contacting surfaces 220, 320 of each of the staple cartridge 200 and anvil plate 300. In this manner, epoxy 250, 350 remains on the tissue contacting surfaces 220, 320 as the buttresses 500a, 500b detach. The epoxy is not implanted into the body but is removed with the stapling apparatus.

Upon full actuation of surgical stapling apparatus 10, a knife 30 associated with surgical stapling apparatus 10 and carried by driver 36 may be utilized to cut tissue "T", as well as surgical buttresses 500a, 500b between the rows of now formed staples 50. Upon movement of anvil plate 300 to the open position spaced apart from staple cartridge 200, surgical buttresses 500a, 500b finish pulling away from tissue contacting surfaces 220, 320 from staple cartridge 200 and anvil plate 300 along the perforations 246, 346.

Figure 8:
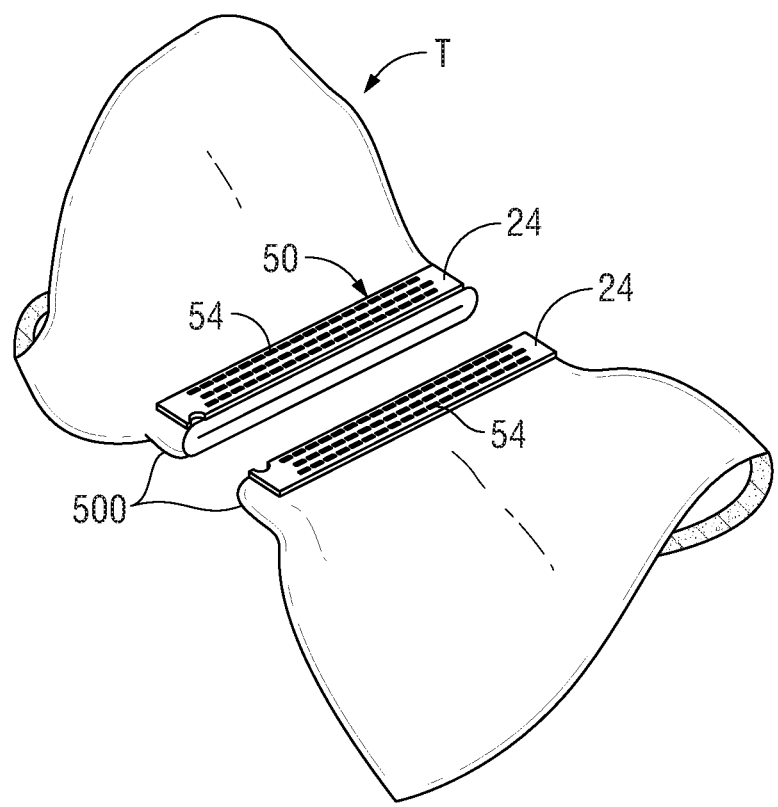
FIG. 8 is a perspective view of the stapled and divided tissue section of FIG. 6.

The resulting tissue "T", divided and stapled closed with staples 50, is illustrated in FIG. 8. Specifically, surgical buttresses 500a, 500b are secured against tissue "T" by legs 56, 58 and backspans 54 of staples 50. Thus, surgical buttresses 500a, 500b are stapled to tissue "T" thereby sealing and reinforcing the staple lines created by staples 50.

Referring now to FIGS. 9A and 9B, an annular surgical stapling apparatus 110, for use with surgical buttresses 124 of the present disclosure, is shown. Surgical stapling apparatus 110 includes a handle assembly 112 having at least one pivotable actuating handle member 133, and an advancing member 135. Extending from handle member 112, there is provided a tubular body portion 114 which may be constructed so as to have a curved shape along its length. Body portion 114 terminates in a staple cartridge 122 which includes a pair of annular arrays of staple retaining slots 152 having a staple 150 disposed in each one of staple retaining slots 152. Positioned distally of staple cartridge 122 there is provided an anvil assembly 120 including an anvil member 121 and a shaft 123 operatively associated therewith for removably connecting anvil assembly 120 to a distal end portion of stapling apparatus 110.

Staple cartridge 122 may be fixedly connected to the distal end of tubular body portion 114 or may be configured to concentrically fit within the distal end of tubular body portion 114. Staple cartridge 122 includes a staple pusher 164 including a proximal portion having a generally frusto-conical shape and a distal portion defining two concentric rings of peripherally spaced fingers (not shown), each one of which is received within a respective staple retaining slot 152.

A knife 130, substantially in the form of an open cup with the rim thereof defining a knife blade 131, is disposed within staple cartridge 122 and mounted to a distal surface of a staple pusher 164. The knife 130 is disposed radially inward of the pair of annular arrays of staples 150. Accordingly, in use, as the staple pusher 164 is advanced, the knife 130 is also advanced axially outward.

Figure 10A:
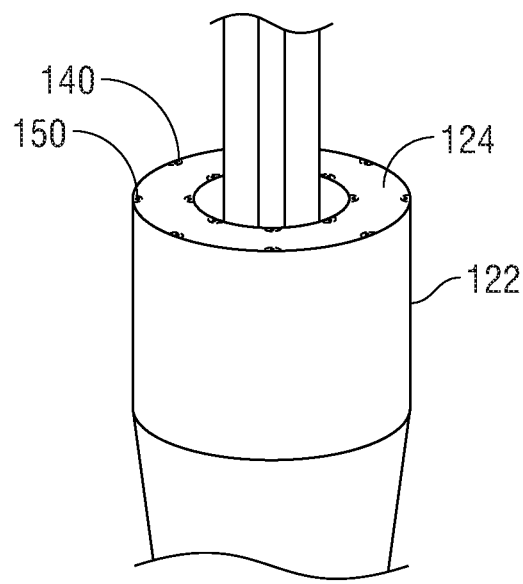
FIG. 10A is a perspective view of an illustrative embodiment of the staple cartridge of the surgical stapling apparatus of FIG. 9A including a surgical buttress in accordance with an embodiment of the present disclosure.

As seen in FIG. 10A, a surgical buttress 124 is releasably attached to the staple cartridge 122 at attachment zones 140 defined by deposits of epoxy 150 disposed between the surgical buttress 124 and the tissue contacting surface 134 of the staple cartridge 122. As described herein above, epoxy 150 bonds the surgical buttress 124 to the tissue contacting surface 134. Perforations 146 surround each deposit of epoxy 150 to allow surgical buttress 124 to release from tissue contacting surface 134. Surgical buttress 124 is provided in an annular configuration and includes a central aperture 125 to receive shaft 123 of anvil assembly 120 therethrough. As illustrated, the attachment zones 140 are concentric in an annular configuration about an outer peripheral edge 162 and inner peripheral edge 160 of staple cartridge 122.

It is envisioned that the surgical buttress 124 may be additionally or alternatively attached or adhered to tissue contacting surface of anvil plate 121 in a manner similar to the surgical buttress 124 attached to staple cartridge 122.

Figure 10B:
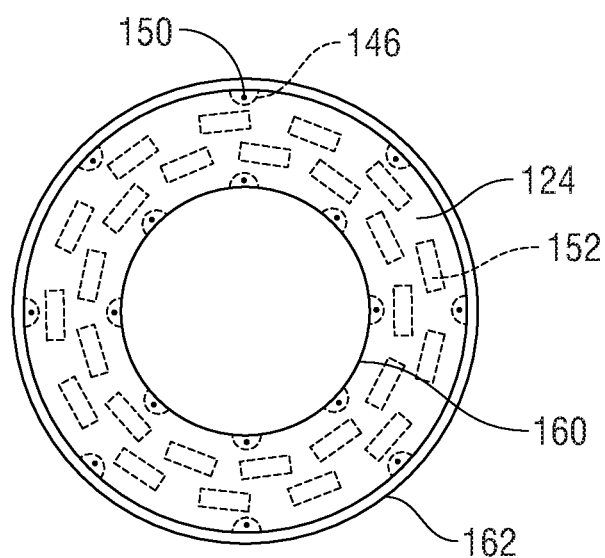
FIG. 10B is a top plan view of the staple cartridge and surgical buttress illustrated in FIG. 10A.

As shown in FIG. 10B, surgical buttress 124 may be secured or adhered to the staple cartridge 122 along an inner portion or peripheral edge 160 and outer portion or peripheral edge 162 of surgical buttress 124. It is envisioned that other configurations may be utilized to retain the surgical buttress 124 to the staple cartridge 122, such as providing the attachment zones 140 along either the inner or outer annular row of staple retaining slots 152, or alternating the attachment zones 140 between the staple retaining slots 152, or among other arrangements within the purview of those skilled in the art.

Figure 11:
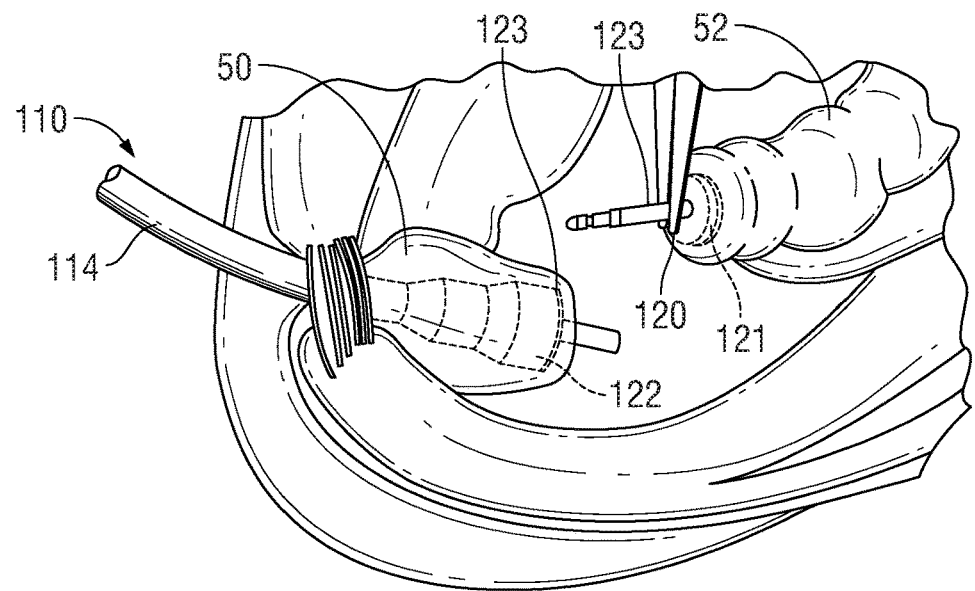
FIG. 11 is perspective view of an intestinal area of a patient, illustrating a method of positioning the anvil rod and staple cartridge of the surgical stapling apparatus of FIGS. 9A, 9B, and 10 within the intestinal area.
Figure 12:
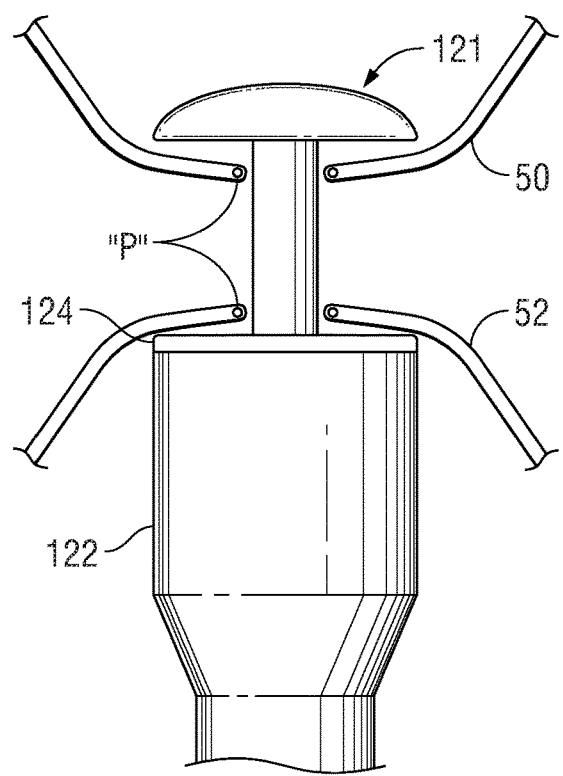
FIG. 12 is a schematic perspective view of the intestinal area of FIG. 11, illustrating the anvil rod mounted to the surgical stapling apparatus.
Figure 13A:
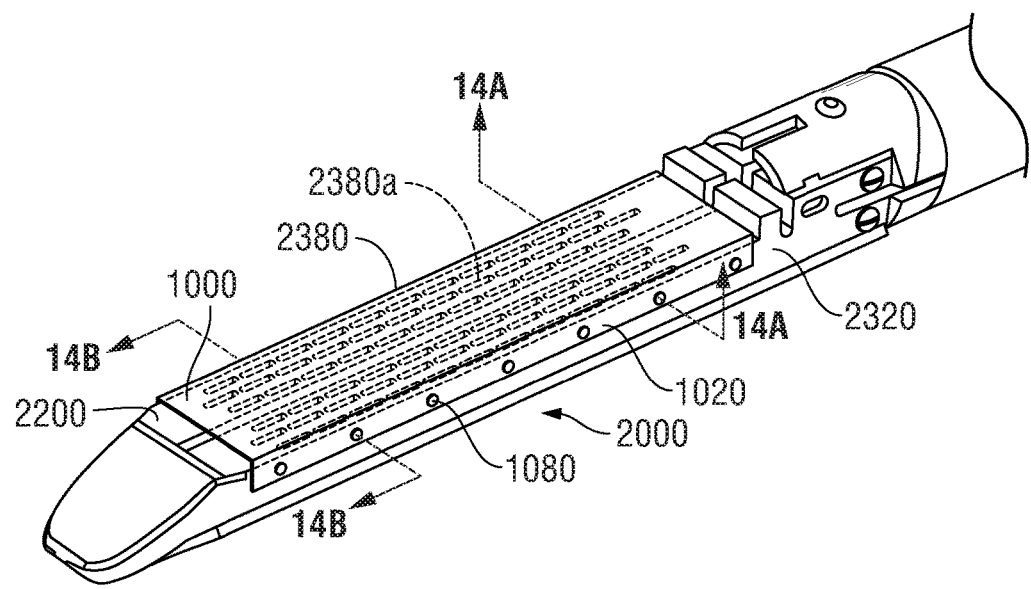
FIG. 13A is a perspective view of an alternate embodiment of a staple cartridge of the surgical stapling apparatus of FIG. 1, illustrating a buttress material supported thereon.
Figure 13B:
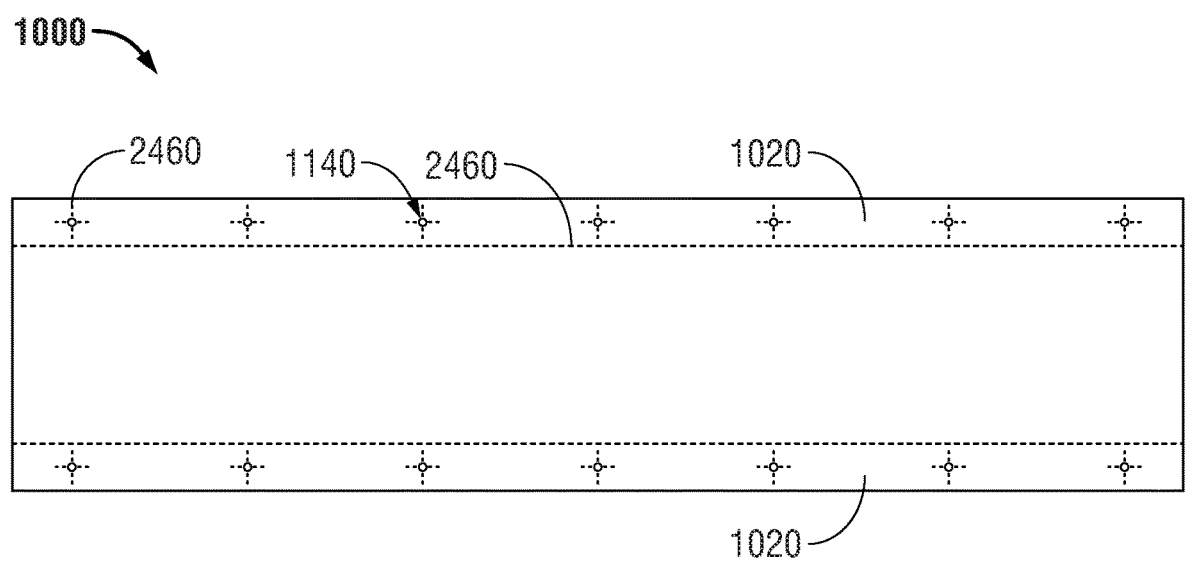
FIG. 13B is a top, plan view of the buttress material of FIG. 13A, illustrating the buttress material unfolded.

Surgical stapling apparatus 110 and detachable anvil assembly 120 are used in an anastomosis procedure to effect joining of intestinal sections 50 and 52. The anastomosis procedure is typically performed using minimally invasive surgical techniques including laparoscopic means and instrumentation. At the point in the procedure shown in FIG. 11, a diseased intestinal section has been previously removed, anvil assembly 120 (optionally including a surgical buttress 124 thereon) has been applied to the operative site either through a surgical incision or transanally and positioned within intestinal section 52, and tubular body portion 114 of surgical stapling apparatus 110 (optionally including a surgical buttress 124 thereon) has been inserted transanally into intestinal section 50. Intestinal sections 50 and 52 are also shown temporarily secured about their respective components (e.g., shaft 123 of anvil assembly 120, and the distal end of tubular body portion 114) by conventional means such as a purse string suture "P", as illustrated in FIG. 12.

Thereafter, the clinician maneuvers anvil assembly 120 until the proximal end of shaft 123 is inserted into the distal end of tubular body portion 114 of surgical stapling apparatus 110, wherein the mounting structure (not shown) within the distal end of tubular body portion 114 engages shaft 123 to effect the mounting. Anvil assembly 120 and tubular body portion 114 are then approximated to approximate intestinal sections 50, 52. Surgical stapling apparatus 110 is then fired. A knife (not shown) cuts the portion of tissue and surgical buttress 124 disposed radially inward of the knife, to complete the anastomosis. The anvil assembly 120 and staple cartridge 122 are opened, with surgical buttress 124 stapled to intestinal sections 50 and 52. Surgical buttress 124 tears away from the deposits of epoxy 150, along perforations 146.

With reference now to FIGS. 13A, 13B, 14A and 14B an alternate embodiment is shown wherein buttress material 1000 is disposed on the tissue contacting surface 2200 of staple cartridge 2000 by a pair of flaps 1020, or margins of material that are positioned adjacent side surfaces 2320 of staple cartridge 2000. Staple cartridge 2000 is similar to staple cartridge 200 discussed hereinabove having tissue contacting surface 2200 and a plurality of retention slots 2380 formed therein for retaining a plurality of staples or fasteners 2400 therein. Any of the embodiments disclosed herein can include the flaps or margins for attaching buttress material.

Buttress material 1000 is disposed on the tissue contacting surface 2200 of staple cartridge 2000 over the openings 2380a of retention slots 2380. Buttress material 1000 includes a pair of flaps 1020 positioned adjacent side surfaces 2320 of staple cartridge 2000 and includes at least one hole 1040 extending through each of flaps 1020. Each hole 1040 is longitudinally spaced apart from the next along the length of a respective flap 1020. Staple cartridge 2000 further includes at least one opening 2480 in each of side surfaces 2320 where each opening 2480 corresponds to a respective one of the holes 1040 of buttress material 1000. In one embodiment, when buttress material 1000 is disposed on tissue contacting surface 2200, holes 1040 of buttress material 1000 substantially align or are in registration with the corresponding openings 2480 of staple cartridge 2000.

Figure 14A:
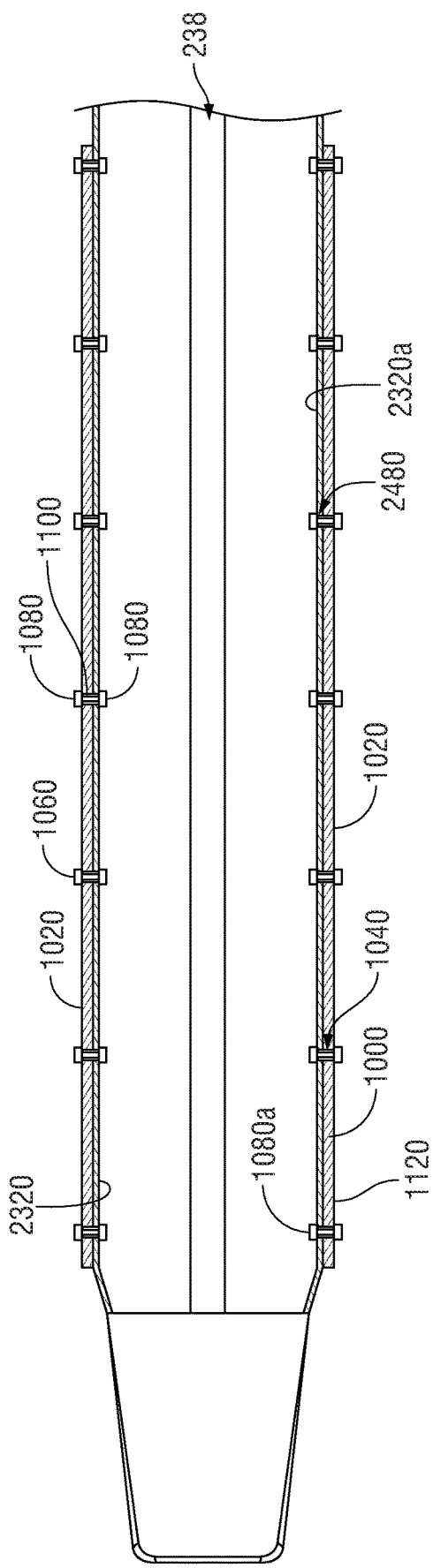
FIG. 14A is a top, cross-sectional view of the cartridge of FIG. 13A, taken along section line 14A-14A of FIG. 13A.
Figure 14B:
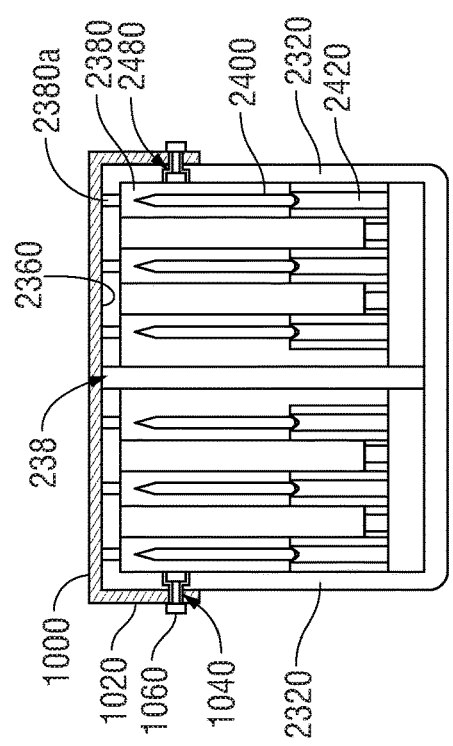
FIG. 14B is a front, cross-sectional view of the staple cartridge of FIG. 13A, taken along section line 14B-14B of FIG. 13A.
Figure 15A:
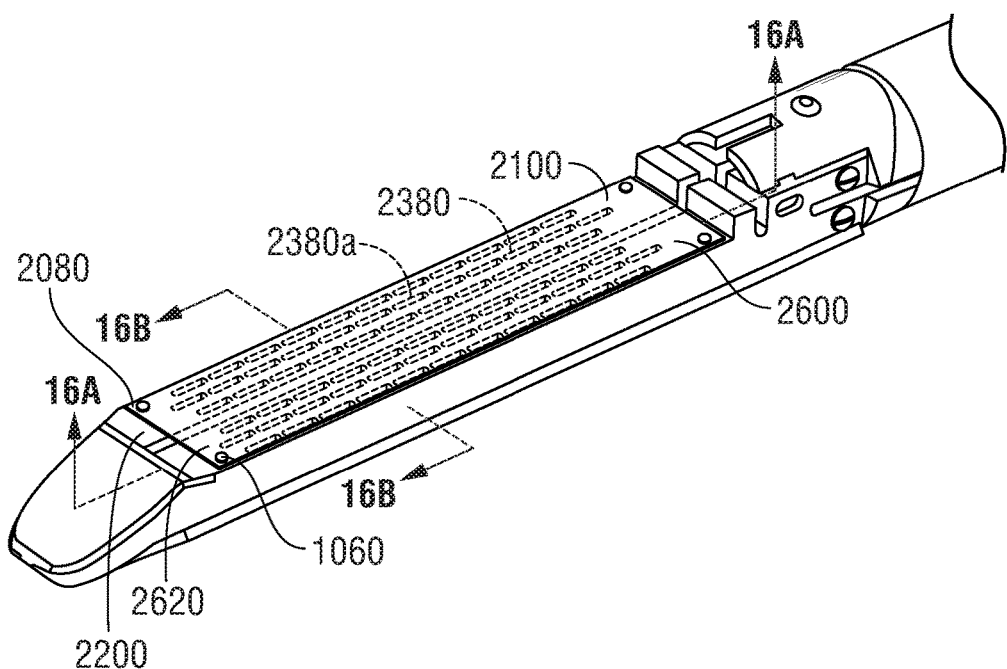
FIG. 15A is a perspective view of another embodiment of a staple cartridge of the annular surgical stapling apparatus of FIG. 1, illustrating a buttress material supported thereon.
Figure 15B:
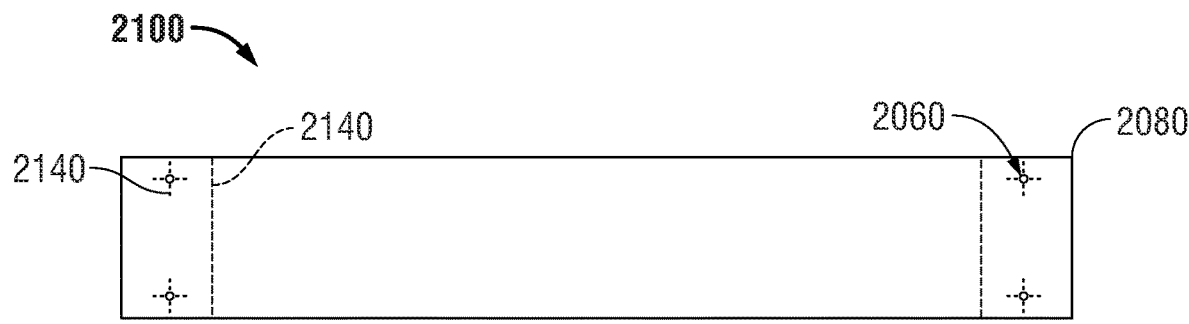
FIG. 15B is a top, plan view the buttress material of FIG. 15A.

With reference now to FIGS. 14A and 14B, a retaining member 1060 extends through each hole 1040 of buttress material 1000 and corresponding opening 2480 of staple cartridge 2000 to secure buttress material 1000 to staple cartridge 2000. Retaining member 1060 includes a pair of buttons 1080 linked together by a shaft or tether 1100. Tether 1100 extends through one of openings 2480 and the corresponding hole 1040 such that a first button 1080a is disposed adjacent an inner surface 2320a of staple cartridge 2000 and a second button 1080b is disposed adjacent an outer surface 1120 of buttress material 1000. Each button 1080 is sized to be larger than a respective opening 2480 or hole 1040 to inhibit removal of the retaining member 1060 from the opening 2480 and hole 1040 during use. The retaining member may have other shapes, including hooks, loops, or tabs. In certain embodiments, the retaining member has bulbous ends that facilitate snapping the retaining member through the holes 2480 and 1040.

Retaining members 1060 may be formed of a bio-compatible or bio absorbable material. In one embodiment, retaining members 1060 may be configured to be brittle and absorbable such that, upon firing of surgical stapling apparatus 10, retaining members 1060 are fractured to release buttress material 1000 from staple cartridge 2000. In another embodiment, retaining members 1060 may be dissolvable upon application of a subsequent fluid by the surgeon or by a surgical instrument, e.g. a saline fluid, during use in order to release buttress material 1000 from staple cartridge 2000. Retaining members 1060 may also or alternatively be dissolvable by body fluids in order to release buttress material 1000. In another embodiment, retaining members 1060 may be formed of an absorbable polymer or other similar low melt temperature material that is configured to melt or soften at body temperature, e.g., about 37° C., to release buttress material 1000 from staple cartridge 2000. In any of the embodiments disclosed herein, retaining members that are integrally formed with the buttress material may be used to attach the buttress to the anvil or staple cartridge of a stapling apparatus.

With reference now to FIGS. 15A, 15B, 16A and 16B, in another embodiment buttress material 2100 is disposed on the tissue contacting surface 2200 of staple cartridge 2000 over the openings 2380a of retention slots 2380. Buttress material 2100 includes a proximal end 2600 and a distal end 2620. Each of proximal and distal ends 2600, 2620 includes at least one hole 2060 and preferably two holes 2060 extending therethrough. For example, in one embodiment, buttress material 2100 may be substantially rectangular with each hole 2060 disposed proximate to a corner 2080 of buttress material 2100. Staple cartridge 2000 further includes at least one opening 2050 through tissue contacting surface 2200 where each opening 2050 corresponds to a respective one of the holes 2060 of buttress material 2100. In one embodiment, when buttress material 2100 is disposed on tissue contacting surface 2200, holes 2060 of buttress material 2100 substantially align or are in registration with the corresponding openings 2050 of staple cartridge 2000.

Figure 16A:
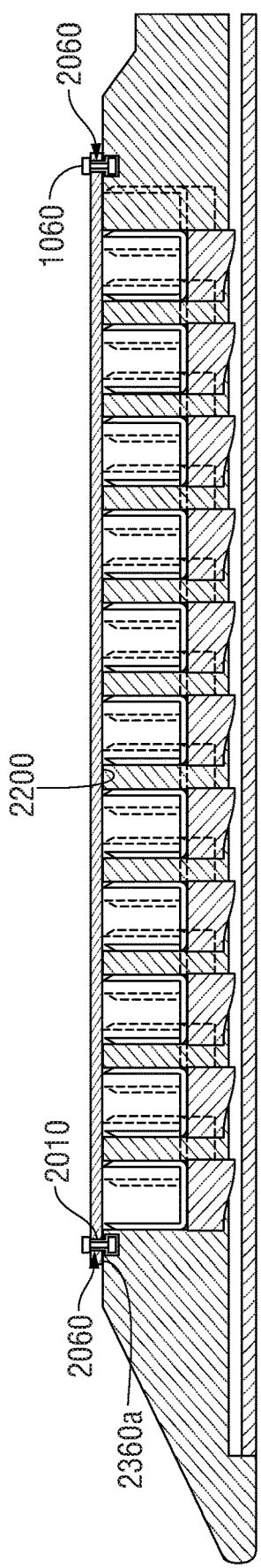
FIG. 16A is a side, cross-sectional view of the staple cartridge of FIG. 15A, taken along section line 16A-16A of FIG. 15A.
Figure 16B:
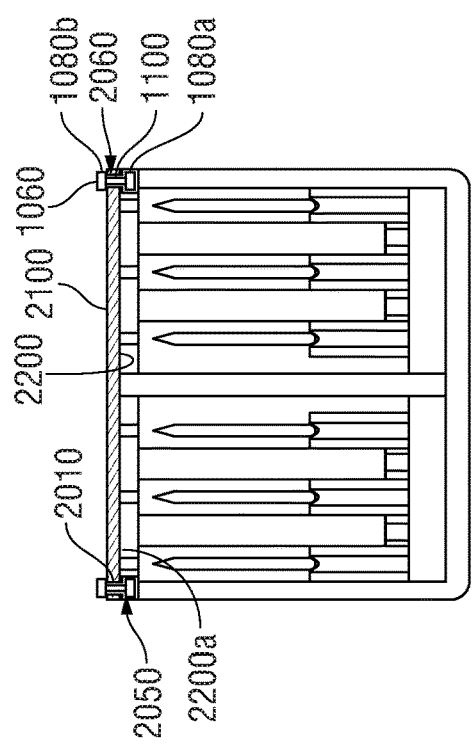
FIG. 16B is a front, cross-sectional view of the staple cartridge of FIG. 15A, taken along section line 16B-16B of FIG. 15A.
Figure 17A:
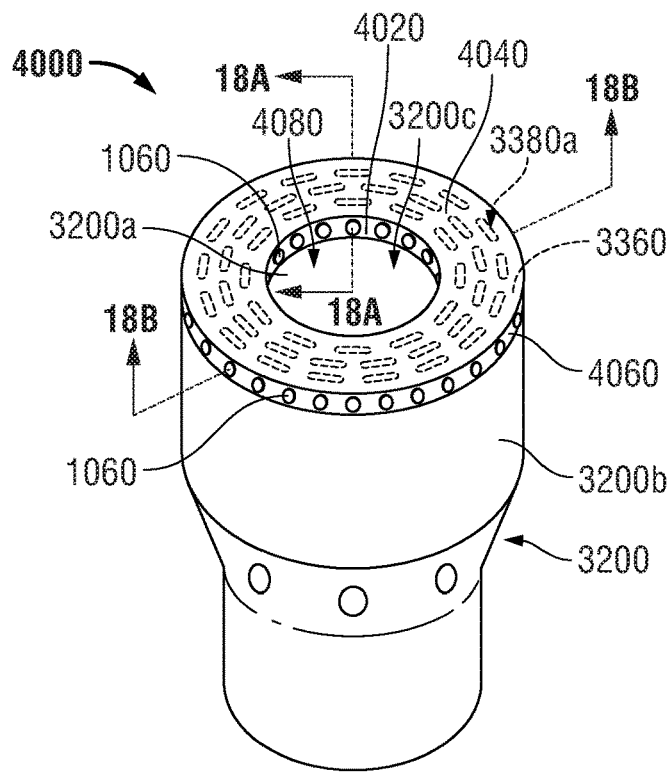
FIG. 17A is a perspective view of another embodiment of a staple cartridge of the annular surgical stapling apparatus of FIGS. 9A-9B, illustrating a buttress material supported thereon.
Figure 17B:
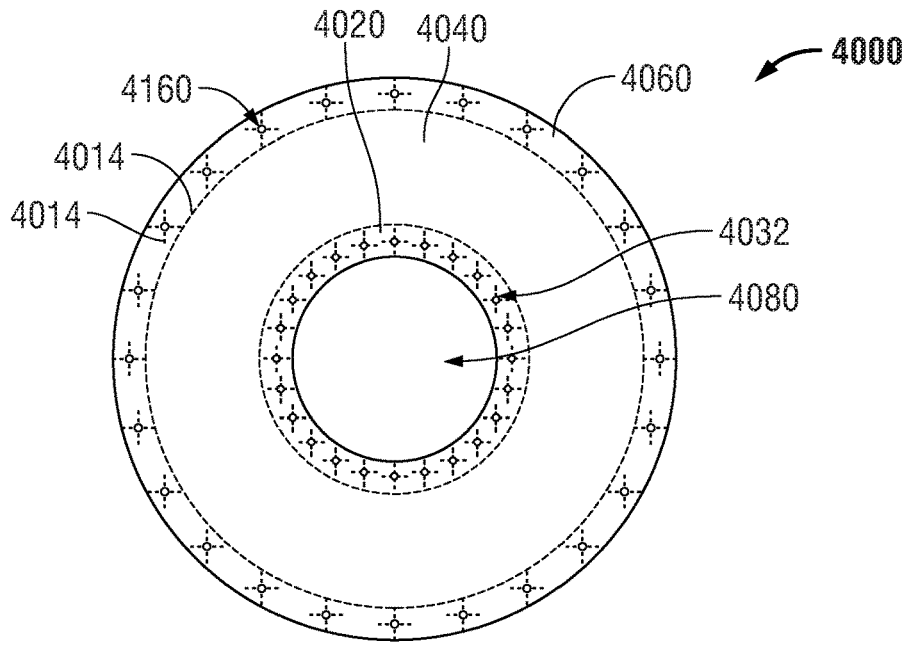
FIG. 17B is a top, plan view the buttress material of FIG. 17A, illustrating the buttress material unfolded.

With reference now to FIGS. 16A and 16B, one of retaining members 1060 extends through each hole 2060 of buttress material 2100 and corresponding opening 2050 of staple cartridge 2000 to secure buttress material 2100 to staple cartridge 2000, as described above. For example, tether 1100 of retaining member 1060 extends through one of openings 2050 and the corresponding hole 2060 such that the first button 1080a is disposed adjacent an inner surface 2200a of tissue contacting surface 2200 and the second button 1080b is disposed adjacent an outer surface 2010 of buttress material 2100. Each button 1080 is sized to be larger than a respective opening 2050 or hole 2060 to inhibit removal of the retaining member 1060 from the opening 2050 or hole 2060 during use.

It is contemplated that a buttress material 1000 or 2100 may also or alternatively be disposed on anvil assembly in the same manner as described above with regard to the attachment of buttress materials 1000 and 2100 to staple cartridge 2000.

With reference now to FIGS. 17A-20B buttress material is shown as generally annular in shape for securing to an annular surgical stapling apparatus 110 as discussed in FIGS. 9A and 9B. Referring now to FIGS. 17A, 17B, 18A and 18B, a buttress material 4000 is generally annular in shape and includes an inner portion 4020, a middle portion 4040, and an outer portion 4060. A substantially centrally located aperture 4080, defined by the inner circumference of inner portion 4020 is formed through buttress material 4000. Buttress material 4000 may be any shape sufficient to provide support for anastomosis of tissue after surgical stapling apparatus 110 has been fired including, for example, a square, a circle, an oval, a triangle or any other polygonal or other shape.

Buttress material 4000 is sized such that when buttress material 4000 is positioned over tissue contacting surface 3360 of staple cartridge 3200, buttress material 4000 extends radially beyond inner surface 3200a and outer surface 3200b of staple cartridge 3200 such that inner portion 4020 and outer portion 4060 of buttress material 4000 may be folded over to abut or engage inner and outer surfaces 3200a, 3200b, respectively.

Each of inner portion 4020 and outer portion 4060 includes an annular array of holes 4412, 4416, respectively, and inner and outer surfaces 3200a and 3200b include corresponding openings 3240, 3260, respectively for the reception of retaining members 1060 therethrough. For example, when buttress 4000 is positioned on tissue contacting surface 3360 with inner and outer portions 4020, 4060 folded over to abut inner and outer surfaces 3200a, 3200b, respectively, the holes 4120, 4160 and the corresponding openings 3240, 3260 may be substantially radially aligned or in registration.

Figure 18A:
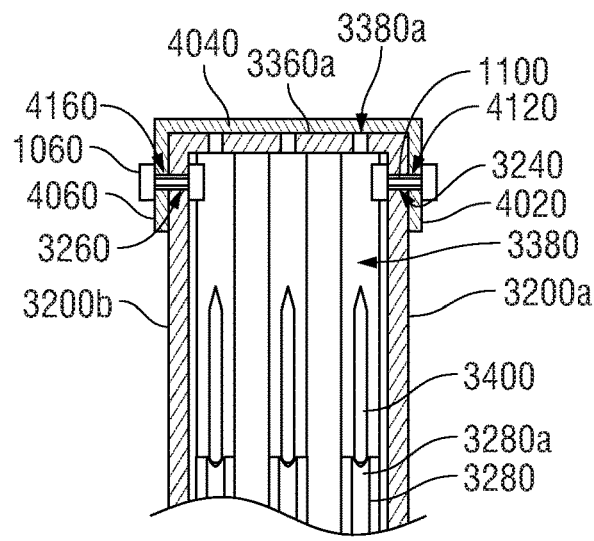
FIG. 18A is a side, cross-sectional view of the staple cartridge of FIG. 17A, taken along section line 18A-18A of FIG. 17A.
Figure 18B:
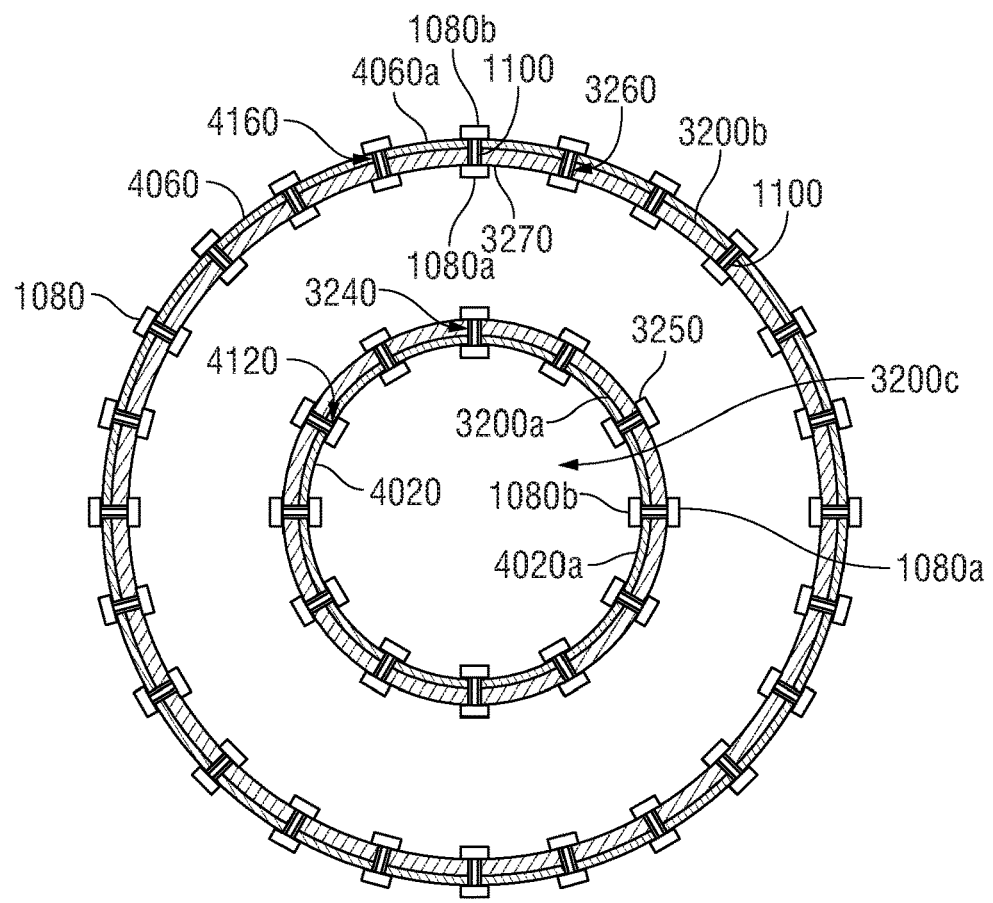
FIG. 18B is a top, cross-sectional view of the staple cartridge of FIG. 17A, taken along section line 18B-18B of FIG. 17A.

With reference now to FIGS. 18A and 18B, one of retaining members 1060 extends through each hole 4120, 4160 of each of inner and outer portions 4020, 4060, respectively and through the corresponding openings 3240, 3260 of staple cartridge 3200 to secure buttress material 4000 to staple cartridge 3200. For example, the tether 1100 of a respective retaining member 1060 extends through one of openings 3240 of inner surface 3200a and through the corresponding hole 4120 of inner portion 4020 of buttress material 4000 such that the first button 1080a is disposed adjacent an inside portion 3250 of inner surface 3200a and the second button 1080b is disposed adjacent an outer surface 4020a of inner portion 4020 of buttress material 4000. Likewise, the tether 1100 of another retaining member 1060 extends through one of openings 3260 of outer surface 3200b and through the corresponding hole 4120 of outer portion 4060 such that the first button 1080a is disposed adjacent an inside portion 3270 of outer surface 3200b and the second button 1080b is disposed adjacent an outer surface 4060a of outer portion 4060. Each button 1080 is sized to be larger than a respective opening 3240, 3260 or hole 4120, 4160 to inhibit removal of the retaining member 1060 from the opening 3240, 3260 or hole 4120, 4160 during use.

With reference now to FIGS. 19A, 19B, 20A and 20B, in one embodiment, a buttress material 5000, formed of similar materials to buttress material 4000, described above, is generally annular in shape and includes an inner portion 5020, a middle portion 5040, and an outer portion 5060. A substantially centrally located aperture 5080, defined by the inner circumference of inner portion 5020 is formed through buttress material 5000. Buttress material 5000 may be any shape sufficient to provide support for anastomosis of tissue after surgical stapling apparatus 110 has been fired including, for example, a square, a circle, an oval, a triangle or any other polygonal or other shape.

Figure 19A:
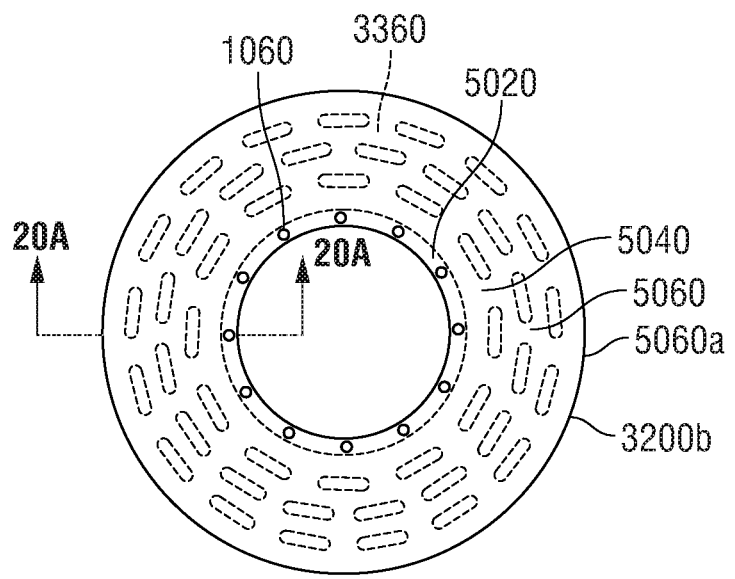
FIG. 19A is a top, plan view of another embodiment of a staple cartridge of the annular surgical stapling apparatus of FIGS. 9A-9B, illustrating a buttress material supported on a flange of the staple cartridge.
Figure 19B:
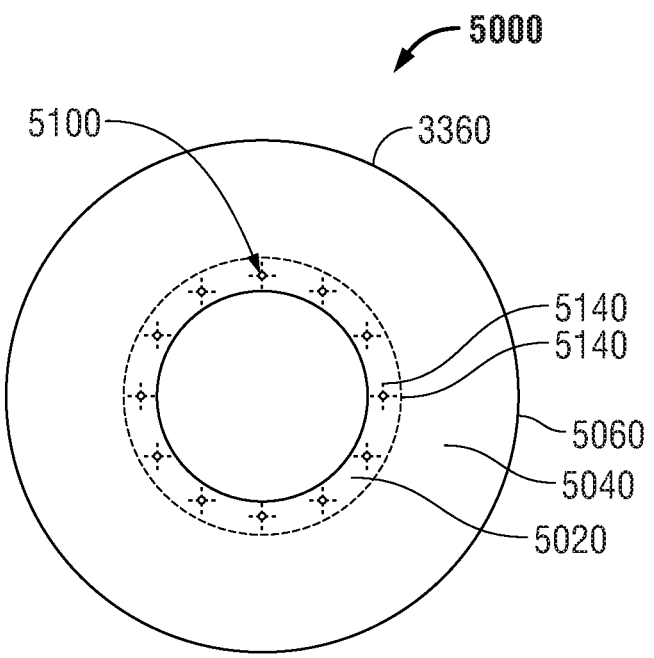
FIG. 19B is a top, plan view the buttress material of FIG. 19A.

With reference now to FIGS. 19A, 19B, and 20A, in one embodiment, buttress material 5000 is sized such that when buttress material 5000 is positioned over tissue contacting surface 3360 of staple cartridge 3200, the outer edge 5060a of outer portion 5060 of buttress material 5000 is substantially aligned with outer surface 3200b of staple cartridge 3200 and inner edge 5020a of inner portion 5020 extends radially inward of the inner surface 3200a of staple cartridge 3200. Staple cartridge 3200 includes a flange 3480 extending radially inward from tissue contacting surface 3360. Inner portion 5020 of buttress material 5000 includes an annular array of holes 5100, and flange 3480 includes a corresponding annular array of openings 3500 for the reception of retaining members 1060 therethrough. For example, when buttress 5000 is positioned on tissue contacting surface 3360 with inner portion 5020 extending radially inward of inner surface 3200a, inner portion 5020 is positioned on flange 3480 and the holes 5100 and the corresponding openings 3500 in flange 3480 may be substantially aligned or in registration, e.g., longitudinally aligned.

One of retaining members 1060 extends through each hole 5100 of inner portion 5020 and through the corresponding openings 3500 of flange 3480 to secure buttress material 5000 to staple cartridge 3200. For example, the tether 1100 of a respective retaining member 1060 extends through one of openings 3500 of flange 3480 and through the corresponding hole 5100 of inner portion 5020 of buttress material 5000 such that the first button 1080a is disposed adjacent a proximal surface 3480a of flange 3480 and the second button 1080b is disposed adjacent a distal surface 5020a of inner portion 5020 of buttress material 5000. Each button 1080 is sized to be larger than a respective opening 3500 or hole 5100 to inhibit removal of the retaining member 106 from the opening 3500 or hole 5100 during use.

With reference now to FIG. 20B, in another embodiment, staple cartridge 3200 may include an inner surface 3520 having a greater radial thickness than inner surface 3200a of staple cartridge 3200 illustrated in FIG. 20A such that a distal portion 3520a of inner surface 3520 of staple cartridge 3200 extends radially inward from tissue contacting surface 3360. Similar to flange 3480 above, distal portion 3520a of inner surface 3520 of staple cartridge 3200 includes an annular array of openings 3540 corresponding to the holes 5100 of buttress material 5000. For example, when buttress 5000 is positioned on tissue contacting surface 3360, inner portion 5020 is positioned on the distal portion 3520a of inner surface 3520 such that the holes 5100 and the corresponding openings 3540 may be substantially aligned, e.g., longitudinally aligned or in registration.

One of retaining members 1060 extends through each hole 5100 of inner portion 5020 of buttress material 5000 and through the corresponding openings 3540 of the distal portion 3520a of the inner surface 3520 of staple cartridge 3200 to secure buttress material 5000 to staple cartridge 3200. For example, the tether 1100 of a respective retaining member 1060 extends through one of openings 3540 of the distal portion 3520a of inner surface 3520 of staple cartridge 3200 and through the corresponding hole 5100 of inner portion 5020 of buttress material 5000 such that the first button 1080a is disposed proximal of the opening 3540 in distal portion 3520a and the second button 1080b is disposed adjacent a distal surface 5020a of inner portion 5020 of buttress material 5000. Each button 1080 is sized to be larger than a respective opening 3540 or hole 5100 to inhibit removal of the retaining member 1060 from the opening 3540 or hole 5080 during use.

Referring now to FIGS. 13A, 15A, 17A and 19A, in any of the above embodiments, buttress materials 1000, 2100, 4000 and 5000 may include perforations or breakaway sections 1140, 2140, 4140, 5140 that are configured to release the buttress material 1000, 2100, 4000, 5000 from the cartridge assemblies 2000, 3200. For example, buttress material 1000 may include perforations extending longitudinally along the fold line of flaps 1020, buttress material 2100 may include perforations extending transverse to the longitudinal axis adjacent the holes 2060 of the proximal and distal portions 2600, 26200, buttress material 4000 may include perforations extending radially along the fold lines of one or both of inner portion 4020 or outer portion 4060, and buttress material 5000 may include an annular array of perforations disposed radially outward of holes 5100 relative to a longitudinal axis of the staple cartridge 3200. Alternatively, or in addition, each of holes 1040, 2060, 4120, 4160 and 5100 may include perforations or break away sections such that buttons 1080a, 1080b of a retaining member 1060 may break through or snap through holes 1040, 2060, 4120, 4160 and 5100 as buttress material 1000, 2100, 4000, 5000 is released from cartridge assemblies 2000, 3200.

Figure 22:
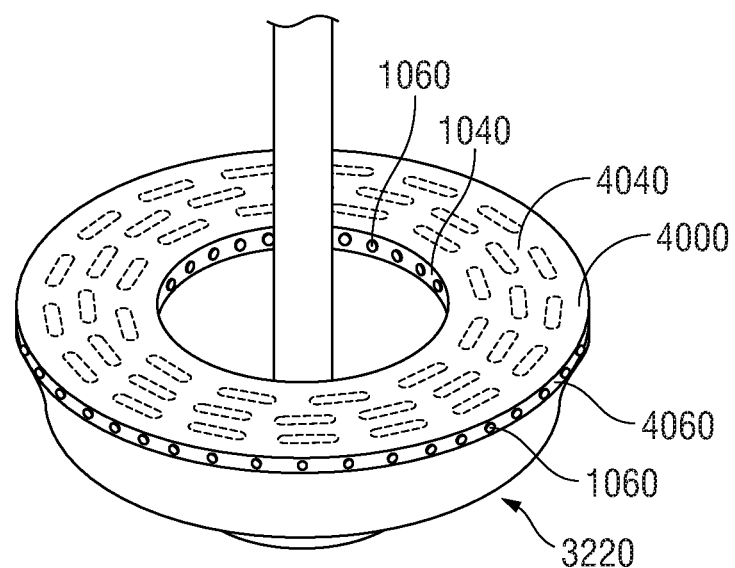
FIG. 22 is a perspective view of a staple cartridge of the annular surgical stapling apparatus of FIGS. 9A-9B, illustrating a buttress material supported thereon in accordance with another embodiment of the present disclosure.

Referring now to FIGS. 21 and 22, in one embodiment, it is contemplated that a buttress material 1000, 2100, 4000 and 5000 may alternatively or additionally be removably secured to one of anvil assemblies 2202, and 3220 in a similar manner as described in the above embodiments for removable securement of buttress materials 1000, 2100, 4000 and 5000 to cartridge assemblies 2000 and 3200.

In one embodiment, retaining members 1060 may be formed during assembly of the surgical stapling apparatus or placement of buttress material to the surgical stapling apparatus 10, 110 during the manufacture or assembly thereof. In a method of attaching the buttress material to a surgical stapling apparatus, the polymer is deposited onto the buttress material, the polymer material having a melting temperature lower than the melting temperature of the buttress material. The polymer can be deposited by injection molding, spraying, dipping, or other methods. In this way, the polymer material can be melted without disrupting the physical properties of the buttress material. In an embodiment of the present disclosure, the degradable polymer material for the attachment features is the polymer used in making Caprosyn™ sutures, also known as L25, which has a melt temperature of about 125 to about 145 degrees celcius, while the buttress material is L41 or L21, which have melting temperatures of about 210 to about 220 degrees celcius and about 185 to about 200 degrees celcius respectively. The L21 polymer is used to make Maxon™ sutures. The polymer L41 is similar to L21, but has a different chemical structure, and has a greater degree of crystallinity and a higher glass transition temperature and melting temperature. Both L21 and L41 are a copolymer of glycolide and trimethylene carbonate.

In certain embodiments, the top of the driver 36 mechanically disrupts the interlocking features of the bonding polymer and may shear off a portion of the polymer material. In certain embodiments, the knife severs off a portion of the polymer material that attaches the buttress material to the apparatus. In certain embodiments, small pushers are provided in the staple cartridge, which are actuated along with the staple firing pushers, to release the buttress material from the apparatus. In further embodiments, additional cutting assemblies can be provided in the anvil, staple cartridge, or both.

In any of the embodiments disclosed herein, the buttress material or the polymer of the attachment zone or attachment feature can be made from glycolic acid, glycolide, lactic acid, lactide, dioxanone, epsilon-caprolactone, trimethylene carbonate, etc., as is known in the art.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A staple cartridge for use with a surgical stapling apparatus, comprising:
    a cartridge body including a tissue contacting surface defining a plurality of staple retaining slots therein, and first and second side surfaces defining respective first and second openings therethrough;
    a buttress material including a body portion overlying the tissue contacting surface of the cartridge body, and first and second flaps extending from the body portion and positioned adjacent to the respective first and second side surfaces of the cartridge body;
    a first retaining member including a shaft extending through the first opening of the first side surface of the cartridge body and through the first flap of the buttress material to releasably retain the buttress material to the cartridge body, the first retaining member including a first button disposed on a first end of the shaft and a second button disposed on a second end of the shaft, the first button positioned adjacent to an inner surface of the first side surface of the cartridge body and the second button positioned adjacent to an outer surface of the first flap of the buttress material, each of the first and second buttons having a diameter larger than a diameter of the shaft; and
    a second retaining member including a shaft extending through the second opening of the second side surface of the cartridge body and through the second flap of the buttress material to releasably retain the buttress material to the cartridge body, the second retaining member including a respective first button disposed on a first end of the shaft and a respective second button disposed on a second end of the shaft, the first button positioned adjacent to an inner surface of the second side surface of the cartridge body and the second button positioned adjacent to an outer surface of the second flap of the buttress material, each of the first and second buttons of the second retainer member having a diameter larger than a diameter of the shaft.

2. The staple cartridge of claim 1, wherein the first flap of the buttress material includes a first hole in registration with the first opening of the first side surface of the cartridge body, and the second flap includes a second hole in registration with the second opening of the second side surface of the cartridge body, the first and second retaining members extending through the respective first and second holes of the buttress material.

3. The staple cartridge of claim 1, wherein the first buttons of the first and second retaining members are larger in size than the respective first and second openings of the cartridge body.

4. The staple cartridge of claim 1, wherein the first and second retaining members are bioabsorbable.

5. The staple cartridge of claim 1, wherein the first and second retaining members are dissolvable.

6. The staple cartridge of claim 1, wherein the first and second retaining members are frangible.

7. The staple cartridge of claim 1, wherein the buttress material includes perforations disposed between the body portion and the first and second flaps along fold lines of the buttress material.

8. The staple cartridge of claim 2, wherein the first and second holes of the buttress material include perforations.

9. The staple cartridge of claim 1, wherein the first and second openings defined in the respective first and second side surfaces of the cartridge body are one of a plurality of first and second openings, and the first and second retaining members are one of a plurality of first and second retaining members.

10. The staple cartridge of claim 1, wherein the cartridge body is a linear and the first and second side surfaces extend longitudinally along a length of the cartridge body on opposed sides of the tissue contacting surface.

11. The staple cartridge of claim 1, wherein the cartridge body is annular and defines a centrally located aperture therein, and the first and second sides of the cartridge body are inner and outer surfaces of the cartridge body.

12. A staple cartridge for use with a surgical stapling apparatus, comprising:
   a cartridge body including a tissue contacting surface defining a plurality of staple retaining slots therein, the tissue contacting surface including proximal and distal portions defining respective first and second openings therethrough;
   a buttress material overlying the tissue contacting surface of the cartridge body; and
   first and second retaining members each including a shaft extending through the respective first and second openings of the cartridge body and through the buttress material to releasably retain the buttress material to the cartridge body, each of the first and second retaining members including a first button disposed on a first end of the respective shaft and a second button disposed on a second end of the respective shaft, the first button positioned adjacent to an inner surface of the tissue contacting surface of the cartridge body and the second button positioned adjacent to an outer surface of the buttress material, each of the first and second buttons of the first and second retaining members having a diameter larger than a diameter of the respective shaft.

13. The staple cartridge of claim 12, wherein the buttress material includes first and second holes in registration with the first and second openings of the cartridge body, the first and second retaining members extending through the respective first and second holes of the buttress material.

14. The staple cartridge of claim 12, wherein the first and second openings defined in the respective proximal and distal portions of the cartridge body are one of a plurality of first and second openings, and the first and second retaining members are one of a plurality of first and second retaining members.

15. The staple cartridge of claim 12, wherein the diameters of the first buttons of the first and second retaining members are larger than diameters of the respective first and second openings of the cartridge body.

16. The staple cartridge of claim 12, wherein each of the first buttons of the first and second retaining members is positioned directly against the inner surface of the tissue contacting surface of the cartridge body.

* * * * *